(12) United States Patent
Ogasawara et al.

(10) Patent No.: US 9,199,095 B2
(45) Date of Patent: Dec. 1, 2015

(54) PARTICLE BEAM IRRADIATION SYSTEM AND OPERATING METHOD

(71) Applicant: HITACHI, LTD., Tokyo (JP)

(72) Inventors: Kosuke Ogasawara, Tokyo (JP); Takuya Nomura, Tokyo (JP); Hideaki Nishiuchi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 14/448,028

(22) Filed: Jul. 31, 2014

(65) Prior Publication Data

US 2015/0060703 A1 Mar. 5, 2015

(30) Foreign Application Priority Data

Aug. 30, 2013 (JP) .................. 2013-180178

(51) Int. Cl.
  *G21K 5/04* (2006.01)
  *A61N 5/10* (2006.01)
  *B01J 19/08* (2006.01)

(52) U.S. Cl.
  CPC ............ *A61N 5/1077* (2013.01); *A61N 5/1048* (2013.01); *B01J 19/081* (2013.01); *A61N 2005/1087* (2013.01); *A61N 2005/1092* (2013.01); *B01J 2219/0801* (2013.01)

(58) Field of Classification Search
  USPC ........ 250/396 R, 397, 398 ML, 492.1, 492.3; 315/500, 501, 503, 506, 507
  See application file for complete search history.

(56) References Cited

U.S. PATENT DOCUMENTS

2005/0139787 A1* 6/2005 Chiba et al. ................ 250/492.3
2014/0187844 A1* 7/2014 Saito et al. ........................ 600/1

FOREIGN PATENT DOCUMENTS

| EP | 1 732 369 A2 | 12/2006 |
|---|---|---|
| EP | 2 140 912 A1 | 1/2010 |
| EP | 2 384 099 A2 | 11/2011 |
| EP | 2 687 262 A1 | 1/2014 |
| JP | 2008-226740 A | 9/2008 |
| JP | 2011-124149 A | 6/2011 |
| JP | 4873563 B2 | 12/2011 |
| JP | 2014-022222 A | 2/2014 |
| JP | 2014-028061 A | 2/2014 |

OTHER PUBLICATIONS

European Search Report received in corresponding European Application No. 14179717.5 dated Jan. 23, 2015.
Chu et al., "Instrumentation for treatment of cancer using proton and light-ion beams", Review of Scientific Instruments, Aug. 1993, vol. 64 No. 8, pp. 2074-2093.
Iwata et al., "Multiple-energy operation with extended flattops at HIMAC", Nuclear Instruments and Methods in Physics Research A, Sep. 2010, No. A624, pp. 33-38.
Arita et al., U.S. Appl. No. 14/090,765, filed Nov. 26, 2013.

* cited by examiner

*Primary Examiner* — Nicole Ippolito
(74) *Attorney, Agent, or Firm* — Mattingly & Malur, PC

(57) ABSTRACT

The operation control data about the component device constituting the synchrotron 13 are structured to include an initial acceleration control data item, a plural extraction control data items, a plural energy change control data items that connect the plural extraction control data items. The plural extraction control data items include extraction condition setting data items and extraction condition cancellation data items corresponding to the plural extraction control data items. As a result, a particle beam irradiation system capable of controlling changes in beam energy, updating operation cycle, and extracting beam in a short time can be provided.

4 Claims, 11 Drawing Sheets

PARTICLE BEAM IRRADIATION SYSTEM AND OPERATING METHOD

BACKGROUND OF THE INVENTION

The present invention relates to a particle beam irradiation system suitable for a particle beam treatment making use of a charged particle beam (ion beam) of protons or heavy ions. More particularly, the invention relates to a particle beam irradiation system capable of controlling changes in beam energy and providing operation cycle updates in a short time, and to an operating method for the system.

The particle beam treatment is known as cancer radiotherapy whereby the affected part of a cancer patient is irradiated with an ion beam of protons or heavy ions for treatment. One method of ion beam irradiation is a scanning irradiation method such as one disclosed in "Review of Scientific Instruments," Vol. 64, No. 8 (August 1993), pp. 2074-2093 (hereinafter, referred to as Non-patent Document 1).

Where a synchrotron is adopted as an ion beam generator for controlling changes in beam energy as required of the scanning irradiation method as a method for providing the control in a short time, there is available a multistage extraction control operation for bringing about irradiation with an ion beam at a plural energy stages within one operation cycle of the ion synchrotron, as disclosed in Japanese Patent No. 4873563 (hereinafter, referred to as Patent Document 1), JP-2011-124149-A (hereinafter, referred to as Patent Document 2), and "Nuclear Instruments and Methods in Physics Research," No. A624 (September 2010), pp. 33-38 (hereinafter, referred to as Non-patent Document 2).

SUMMARY OF THE INVENTION

With the scanning irradiation method, the control of irradiation aimed at an irradiation field (referred to as the layer hereunder) in the depth direction of the affected part is implemented by controlling the energy of an irradiation ion beam. For this reason, it is necessary to bring about rapidly the changes in the energy of the ion beam supplied from the ion beam generator in order to enhance the dose rate in effect when the irradiation scanning method is applied. Also with the scanning irradiation method, it is necessary to control the energy of beam irradiation in accordance with the tumor volume (depth from the body surface). This requires suitably controlling the combination of irradiation beam energy stages with regard to each patient or each affected part to be irradiated.

Where the synchrotron is adopted as the ion beam generator, a series of operations such as injection, acceleration, extraction and deceleration are controlled as one operation cycle. Where control of the changes in ion beam energy is performed repeatedly as in the case of the scanning irradiation method, the synchrotron needs to have the operation cycle updated every time, so that it takes time to change the ion beam energy. As a countermeasure against this problem, Patent Document 1 and Non-patent Document 2 describe the multistage extraction operation whereby the beam is extracted at the plural energy stages within one operation cycle. For example, Non-patent Document 2 shows that the affected part can be irradiated with the beam at all energy stages in one round of operation control when there is prepared operation control data that integrates into one range all energy ranges available for irradiation by the synchrotron and when the beam is extracted by extending the flat top period only with the energy for beam irradiation. Further, since the beam is available for irradiation at all energy stages in one round of operation control, the synchrotron can always implement irradiation by use of the same operation control data. This provides the advantageous effect of simplifying the operation control of the synchrotron in a particle beam treatment system.

However, to implement operation control effectively, as described in Patent Document 1 and Non-patent Document 2 requires that the amount of accumulated beam charge of the synchrotron be sufficient for irradiating the affected part with the entire energy for irradiation in one operation cycle. For example, if for some reason the amount of accumulated beam charge necessary for treatment irradiation is not available under acceleration control of the synchrotron, the accumulated beam charge will be exhausted halfway through a preset irradiation energy range. If the accumulated beam charge in the synchrotron is exhausted, it is necessary to interrupt ion beam irradiation for the sake of transition from extraction control to deceleration control in order to update the operation control of the synchrotron. Where use is made of the operation control data that integrates into one range all energy ranges available for irradiation by the synchrotron, direct transition from extraction control at the extraction energy to deceleration control cannot be made because of the need to ensure the continuity of set values. For this reason, the energy change control data ranging from extraction control at the extraction energy to deceleration control needs to be updated. The time required to perform the transition from extraction control at the extraction energy to deceleration control is one factor that lowers the dose rate and makes it difficult to shorten treatment time. Likewise, direct transition from extraction control at the extraction energy to deceleration control cannot be performed when ion beam irradiation is interrupted due to a failure in the component devices making up the particle beam treatment system.

Where use is made of the operation control data that integrates into one range all energy ranges available for irradiation by the synchrotron and where irradiation conditions are in effect involving a narrow absorbed dose range fit for the thickness of the affected part (called the Spread-Out Bragg Peak, abbreviated to SOBP hereunder), there is a tendency that it takes a longer time to perform controls ranging from injection beam energy to irradiation start energy and from irradiation end energy to deceleration end energy on the synchrotron, which amounts to a wasteful time not contributing to beam irradiation, as compared with the time required for beam irradiation. This is another factor that lowers the dose rate and makes it difficult to shorten treatment time. Since the SOBP varies with each patient and with each affected part, it is necessary to select the irradiation energy stage needed to form a suitable SOBP as synchrotron operation control data and to control the updates of the operation control data reflecting the selected irradiation energy.

Patent Document 2 describes a controller of an accelerator equipped with a magnetic field reference generation unit that outputs information on magnetic flux density corresponding to elapsed time with reference to a coil current which excites a magnetic field coil of the accelerator, and a current reference conversion unit that obtains a coil current which generates the magnetic field corresponding to the magnetic flux density information. The magnetic flux density information output by the magnetic field reference generation unit is then output in a combination of four patterns (initial rise pattern, decrease pattern, increase pattern, and completion pattern) by a control method that implements beam extraction at the plural energy stages within one operation cycle. According to Patent Document 2, ion beam extraction is made available at the plural energy stages in one operation cycle by suitably combining the four magnetic flux density patterns. On the basis of this feature, it is possible to select an irradiation energy stage necessary for forming an appropriate SOBP. On the other hand, the timings for selecting and outputting the four patterns are written beforehand in a timing controller so that, as in the case of Patent Document 1 and Non-patent Document 2, direct transition from extraction control at the extraction energy to deceleration control cannot be performed when ion beam irradiation is interrupted. The problem still remains that unless the energy change control data ranging from extraction control at the extraction energy to deceleration control is updated, the transition to deceleration control (referred to as the completion pattern in Patent Document 2) cannot be performed.

It is therefore an object of the present invention to provide a particle beam irradiation system and an operating method for the system whereby an operation cycle is updated in a short time upon interruption of ion beam irradiation during a multistage extraction control operation for rapidly implementing the control of changes in the energy of the beam extracted from the synchrotron, so that the dose rate will be improved.

Another object of the present invention is to provide a particle beam irradiation system and an operating method for the system whereby beam irradiation is performed over a desired energy range in a short operation cycle during a multistage extraction control operation for rapidly implementing the control of changes in the energy of the beam extracted from the synchrotron, so that the dose rate will be improved.

A further object of the present invention is to provide a particle beam irradiation system and an operating method for the system whereby beam loss is reduced in an energy change interval during a multistage extraction control operation for rapidly implementing the control of changes in the energy of the beam extracted from the synchrotron, so that the dose rate will be improved.

In achieving the foregoing and other objects of the present invention and according to one embodiment thereof, there is provided a particle beam irradiation system including: a synchrotron accelerating an ion beam and having the accelerated ion beam extracted therefrom; an irradiation device for executing irradiation with the ion beam extracted from the synchrotron; and a controller for causing operation control data about component devices making up the synchrotron to be formed by at least one initial acceleration control data item, a plural extraction control data items for ion beam extraction at a plural energy stages, a plural energy change control data items connecting the plural extraction control data items, and a plural deceleration control data items corresponding to the plural extraction control data items, the controller further combining the control data items to provide beam extraction control at the plural energy stages. The controller holds, as the plural extraction control data items, extraction condition setting data items for setting extraction conditions and extraction condition cancellation data items for canceling the extraction conditions.

According to the present invention, beam irradiation at a desired irradiation energy stage can be performed in a short time, which shortens treatment time and improves the dose rate.

Also according to the present invention, beam loss other than that during a beam irradiation period can be reduced, which enhances the efficiency of beam utilization. The enhanced efficiency of beam utilization in turn shortens treatment time and improves the dose rate.

DESCRIPTION OF THE PREFERRED EMBODIMENTS

Some preferred embodiments of the present invention are explained below with reference to the accompanying drawings.

Figure 1:
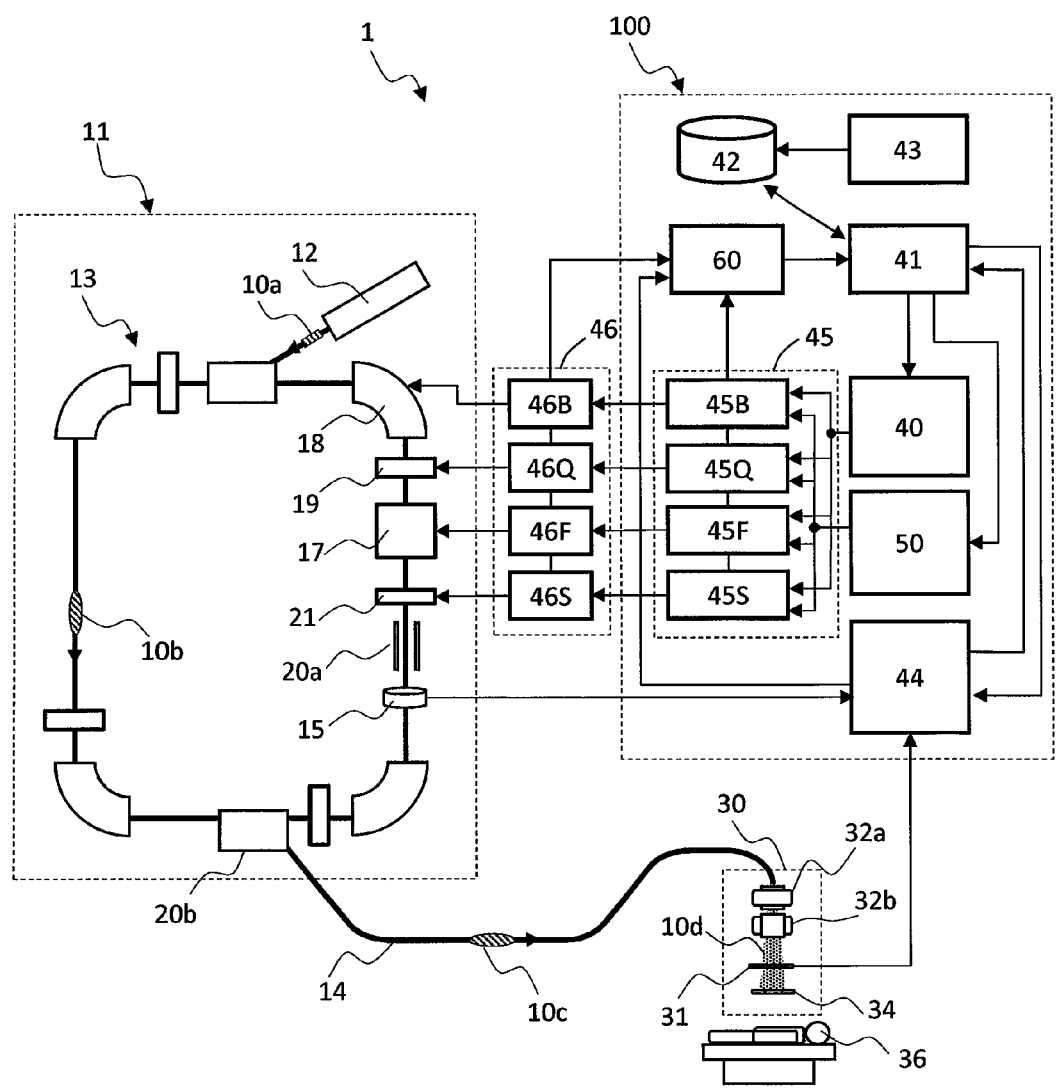
FIG. 1 is a diagram showing a configuration of a particle beam irradiation system as one preferred embodiment of the present invention.

FIG. 1 is a diagram showing a configuration of a particle beam irradiation system as one preferred embodiment of the present invention.

As shown in FIG. 1, the particle beam irradiation system 1 of this embodiment includes an ion beam generator 11, a beam transport device 14, and an irradiation field forming apparatus (charged particle beam irradiation apparatus, simply called the irradiation apparatus hereunder) 30. The beam transport device 14 connects the ion beam generator 11 with the irradiation apparatus 30 installed inside a treatment room.

The ion beam generator 11 includes an ion source (not shown), a preaccelerator 12, and a synchrotron 13. The ion source is connected to the preaccelerator 12 that in turn is connected to the synchrotron 13. The preaccelerator 12 accelerates an ion beam 10 generated from the ion source up to an energy stage high enough for the beam to be injected into the synchrotron 13. The ion beam 10a accelerated with the pre-accelerator 12 is injected into the synchrotron 13.

The synchrotron 13 includes a radio frequency accelerator (radio frequency accelerating cavity) 17 that applies a radio frequency to an ion beam 10b circulating along a circular path for acceleration up to a target energy stage, a radio frequency extraction electrode 20a that increases a betatron vibration amplitude of the circulating ion beam 10b, and an extraction deflector 20b that takes the ion beam 10b out of its circular path.

The ion beam 10b injected into the synchrotron 13 is accelerated to a desired energy stage when supplied with the energy of the acceleration radio frequency applied to the radio frequency accelerator 17. At this point, as the circulating energy of the ion beam 10b is being raised, the magnetic field intensities of a bending magnet 18, a quadrupole magnet 19, and a sextupole magnet 21 together with the frequency of the radio frequency voltage applied to the accelerating cavity 17 are increased correspondingly so that the circular path of the ion beam 10b circulating inside the synchrotron 13 remains constant.

After the ion beam 10b has been accelerated to the desired energy stage, control is performed to set extraction conditions so as to regulate the excitation amounts of the quadrupole magnet 19 and sextupole magnet 21 in a manner establishing the conditions under which the circulating ion beam 10b can be extracted (i.e., stability limit conditions for the circulating beam). Upon completion of extraction condition setting control, an extraction radio frequency voltage is applied to the radio frequency extraction electrode 20a in order to increase the betatron vibration amplitude of the ion beam 10b circulating inside the synchrotron 13. The increase in the betatron vibration amplitude causes the circulating ion beam 10b having exceeded the stability limit conditions to be extracted from the synchrotron 13 toward the beam transport device 14. The beam transport device 14 transports the extracted ion beam to the irradiation apparatus 30. Control of beam extraction from the synchrotron 13 can be implemented at high speed by turning on and off the radio frequency voltage applied to the radio frequency extraction electrode 20a.

Upon completion of the control of beam extraction from the synchrotron 13, control is performed to cancel the extraction conditions so as to regulate the excitation amounts of the quadrupole magnet 19 and sextupole magnet 21 in a manner canceling the stability limit conditions established for the circulating ion beam 10b at the time of setting the extraction conditions.

Upon completion of extraction condition cancellation control, the ion beam 10b circulating inside the synchrotron 13 is decelerated by lowering the magnetic field intensities of the bending magnet 18, quadrupole magnet 19, and sextupole magnet 21 together with the frequency of the radio frequency voltage applied to the accelerating cavity 17. Transition to the next operation cycle is thus performed.

The irradiation apparatus 30 controls an ion beam 10c guided by the beam transport device 14 so as to irradiate an affected part 37 of a patient 36 on the treatment couch in conformity with the shape of the affected part 37 and its depth from the patient's body surface.

The irradiation apparatus 30 operates by the scanning irradiation method, such as one Non-patent Document 1 (see page 2086, FIG. 45). Because the scanning irradiation method allows the affected part 37 to be irradiated directly with an ion beam 10d, the efficiency of ion beam utilization is high. This method further permits irradiation of the affected part with the ion beam 10d in a manner more conforming to the affected part shape than the existing scattering irradiation method.

The irradiation range in the depth direction of the affected part 37 is adjusted by changing the energy stage of the ion beam 10, whereby the desired affected part 37 is irradiated. Particularly with the scanning irradiation method, the ion beam 10b circulating inside the synchrotron 13 is adjusted in energy before being extracted so as to adjust the irradiation range of the ion beam 10 to the depth of the affected part 37. This requires changing the energy stage a number of times during radiation treatment of the patient 36. The methods for irradiating the affected part with the beam in the planar direction include a spot scanning irradiation method and a raster scanning irradiation method. According to the spot scanning irradiation method, the irradiation plane of the affected part 37 is divided into dose-managed regions called spots; scanning is stopped at each spot to irradiate it with the beam until a predetermined dose 311 is reached. The beam is then stopped at that point, and the next spot is reached for irradiation. In this manner, the spot scanning irradiation method involves updating the irradiation starting position at each spot. According to the raster scanning irradiation method, the dose-managed regions are set as with the spot scanning irradiation method. However, beam scanning is not stopped on a spot-by-spot basis. Instead, the scanning path is being scanned with the beam for irradiation. For this reason, the uniformity of irradiation doses is improved by execution of repainting irradiation whereby irradiation is repeated at a reduced dose per round of irradiation. Thus the raster scanning irradiation method involves updating the irradiation starting position per scanning path. Under control with the spot scanning method, as with the raster scanning method, the dose per round of irradiation at each spot may be set low and the irradiation plane may be scanned a number of times until an ultimate target dose is reached.

Figure 2:
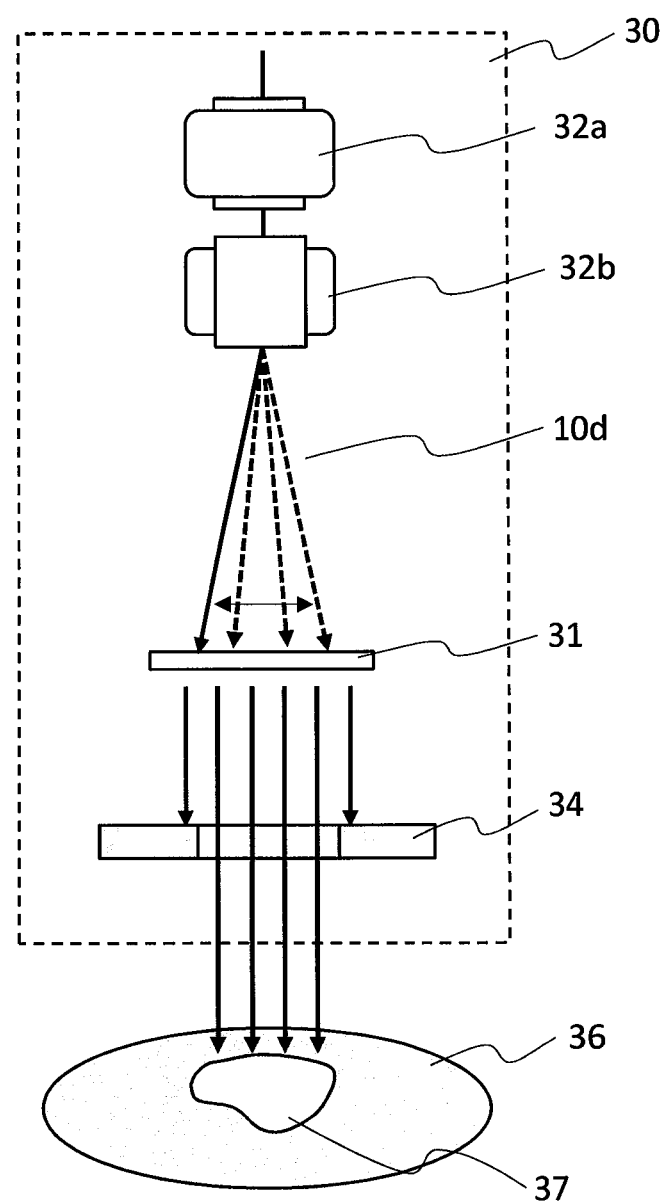
FIG. 2 is a diagram showing a structure of an irradiation device operating by a scanning irradiation method as one embodiment of the present invention.

FIG. 2 shows a structure of the irradiation apparatus 30. The irradiation apparatus 30 has scanning magnets 32a and 32b. The scanning magnets 32a and 32b allow the affected part plane to be scanned with the beam in conformity with the shape of the affected part. The irradiation apparatus 30 also has a dose monitor 31 that measures the dose 311 of the ion beam 10d with which the patient 36 is irradiated, and a beam shape monitor (not shown). These devices are used successively to monitor the dose and the shape of the ion beam 10d for irradiation. The ion beam 10d subjected to scanning with the scanning magnets 32 forms an irradiation field through a collimator 34 in conformity with the affected part 37 of the patient 36.

Returning to FIG. 1, the particle beam irradiation system 1 of this embodiment is equipped with a control system 100 (controller). The control system 100 includes: an accelerator controller 40 that controls the ion beam generator 11 and beam transport device 14; a main controller 41 that integrally controls the particle beam irradiation system 1 as a whole; a treatment planning device 43 that plans beam irradiation conditions for the patient 36; a data storage device 42 that stores the information planned by the treatment planning device 43 as well as control information regarding the synchrotron 13 generating the ion beam and the beam transport device 14; an irradiation controller 44 that controls the component devices making up the irradiation apparatus 30 and the dose of the ion beam 10d with which the affected part 37 is irradiated; a timing system 50 that provides synchronizing control over the component devices making up the synchrotron 13; an interlock system 60 that remains independent of the main controller 41 so as to guarantee the safety of the patient 36; and a power supply controller 45 that controls a power supply 46 for the component devices making up the synchrotron 13. The data storage unit 42 may be provided as part of the main controller 41.

The power supply 46 is a collective term representing the power supplies for the plural devices making up the synchrotron 13. Shown in FIG. 1 as the power supplies of the plural devices are a power supply 46B of the bending magnet 18, a power supply 46Q of the quadrupole magnet 19, a power supply 46S of the sextupole magnet 21, and a power supply 46F of the accelerating cavity 17. As with the power supply 46, the power supply controller 45 is a collective term representing plural power supply controllers corresponding to the plural power supplies of the component devices. Shown in FIG. 1 are a controller 45B of the power supply 46B, a controller 45Q of the power supply 46Q, a controller 45S of the power supply 46S, and a controller 45F of the power supply 46F.

Figure 9:
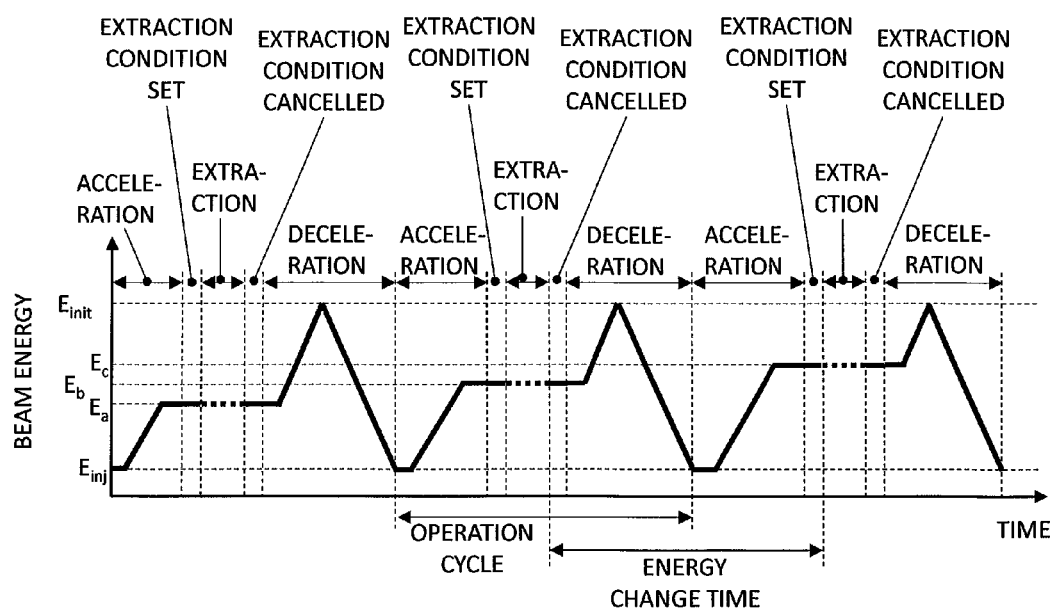
FIG. 9 is a diagram showing an operation sequence of an ordinary synchrotron.

Explained below are some of the items studied by the inventors with reference to the above-cited literature. FIG. 9 shows an operation sequence of the ordinary synchrotron 13.

The synchrotron 13 performs a series of controls including acceleration, extraction, and deceleration in one operation cycle. Before and after extraction control, specific controls are needed; before extraction control, control is required to set the extraction conditions necessary for extracting the ion beam 10b from the synchrotron 13; after extraction control, control is required to cancel the extraction conditions.

Where the ordinary synchrotron 13 is controlled in operation, control data corresponding to the series of controls are stored as pattern data in a memory of the power supply controller 45. The power supply controller 45 updates the control data on the basis of a timing signal 51 output from the timing system 50 that manages the control timings of the component devices making up the synchrotron 13.

As shown in FIG. 9, the synchrotron 13 performs controls ranging from acceleration to deceleration in one operation cycle. For this reason, to change the energy stage of the ion beam 10c to be extracted requires updating the operation cycle after the remaining beam is decelerated by making transition to deceleration control upon completion of extraction control. After the operation cycle is updated, the ion beam 10b is again accelerated to implement control for changing to the desired energy stage.

As a result, where the ordinary synchrotron 13 is controlled in operation, it takes almost as much time to change the energy stage of the ion beam 10b as one operation cycle. This prolongs treatment time and poses problems in improving the dose rate.

As a countermeasure against such problems, there has been proposed the multistage extraction operation whereby a beam is extracted at the plural energy stages in one operation cycle, as discussed in Patent Documents 1 and 2, and Non-patent Document 2.

Patent Document 1 discloses the multistage extraction control operation of the ion synchrotron whereby the ion beam 10 is extracted at the plural energy stages within one operation cycle. This type of multistage extraction control operation helps shorten the time required to change the energy stage by the scanning irradiation method.

Non-patent Document 2 describes how stepped operation control data formed by energy change and extraction controls and corresponding to the plural energy stages extracted from the ion synchrotron are prepared beforehand (page 34, FIG. 2), and how operations are carried out (page 35, FIG. 3) to extend the flat portion of the operation control data regarding an extraction control unit and corresponding to the energy stage of the ion beam to be extracted.

As explained in Non-patent Document 2, if control is performed whereby the operation control data permitting extraction at the plural energy stages are prepared beforehand as the pattern data and if the ion beam necessary for completing all irradiation has been accumulated in the synchrotron, the explained arrangement provides the effect of completing irradiation at all energy stages in one operation cycle. However, if the ion beam necessary for completing all irradiation has not been accumulated in the synchrotron, it is necessary to perform deceleration control when the ion beam is exhausted, before updating the operation cycle to again inject and accelerate the ion beam 10b. At this point, to make transition from energy extraction control with the exhausted ion beam 10 to deceleration control requires taking into account the continuity of the operation control data. That in turn requires updating all operation control data for energy change control stored subsequent to the energy stage at which the ion beam 10b was exhausted. Direct transition cannot be made to deceleration control from extraction control using the operation control data in question. For this reason, it takes an inordinate time to update the operation cycle of the synchrotron 13. Also, in the event of a failure in any one of the component devices making up the particle beam irradiation system 1, the problem remains that direct transition cannot be made from extraction control using the operation control data to deceleration control.

Patent Document 2 describes the controller of the accelerator equipped with the magnetic field reference generation unit that outputs magnetic flux density information corresponding to elapsed time with reference to the coil current which excites the magnetic field coil of the accelerator, and the current reference conversion unit that obtains the coil current which generates the magnetic field corresponding to the magnetic flux density information. The magnetic flux density information from the magnetic field reference generation unit is output in a combination of four patterns (initial rise pattern, decrease pattern, increase pattern, and completion pattern) by a control method that implements beam extraction at the plural energy stages within one operation cycle. According to Patent Document 2, the ion beam 10 can be extracted at the plural energy stages in one operation cycle by suitably combining the four magnetic flux density patterns. Meanwhile, the timing signals that command the combination sequences of the four patterns by selecting the operation control data on the synchrotron are written beforehand in the timing controller. As a result, direct transition from extraction control at the extraction energy to deceleration control cannot be made so as to guarantee the continuity of set values. Because rapid deceleration control is not available when the beam is exhausted or in the event of a device failure, it takes time to update the operation cycle of the synchrotron. Since a current reference converter is used successively to calculate and output the exciting currents of the bending magnet and quadrupole magnet, operation parameters need to be changed every time the pattern is changed. This poses the problem of complicating the equipment configuration and control arrangements.

Further, Non-patent Document 2 describes preparing the operation control data that integrate into one range all energy ranges available for irradiation by the synchrotron, and extracting the beam by extending the flat top period only with the energy for beam irradiation.

By the existing method of the multistage extraction operation, as outlined above, the beam is accelerated up to the initial extraction energy stage and extracted, followed by a change to the next irradiation energy stage without transition to deceleration control. With the energy stage changed, the beam is extracted followed by a change to the next irradiation energy stage. In this manner, beam extraction and energy change are carried out repeatedly. Thus at the time of energy change, the operation needs to be performed in a manner preventing beam loss.

For example, the synchrotron described in Non-patent Document 2 prepares the operation control data that integrates into one range all energy ranges available for irradiation by the synchrotron, and has the beam extracted by extending the flat top period only with the energy for beam irradiation. For this reason, those excitation patterns of the quadrupole magnet and sextupole magnet which form the beam extraction conditions upon energy change reflect the excitation amounts corresponding to the next irradiation energy stage without canceling the extraction conditions. The data structure is continued from that of acceleration control patterns.

However, performing energy change control without canceling the extraction conditions can cause beam loss upon energy change. Thus according to Non-patent Document 2, a quadrupole magnet (QDS) that controls the extraction conditions is prepared apart from the above-mentioned quadrupole magnet. The extraction conditions are then set by adding up the excitation amount of the additionally prepared quadrupole magnet (QDS) and that of the quadrupole magnet for stably accelerating the beam and having the accelerated beam extracted from the synchrotron. Thus the beam extraction conditions are set by having the quadrupole magnet (QDS) excited, and are cancelled by stopping the excitation of the quadrupole magnet (QDS).

In this manner, preparing the quadrupole magnet (QDS) makes it possible to set and cancel the extraction conditions upon multistage extraction control. However, because of the need to set up the quadrupole magnet (QDS) in addition to the quadrupole magnet for implementing the ordinary functions necessary for synchrotron performance, the increase in synchrotron size is inevitable, and so is the costs. The present invention concerns a multistage extraction control operation whereby the ion beam 10 can be extracted from an ion synchrotron at a plural energy stages in one operation cycle, and provides an ion synchrotron capable of performing the control of beam energy change and updating the operation cycle in a short time. The details of the invention are explained below.

Explained first with reference to FIG. 3 through FIGS. 7A and 7B are the structure of control data in effect in the multistage extraction operation characteristic of this embodiment, and the operation sequence that uses the control data.

Figure 3:
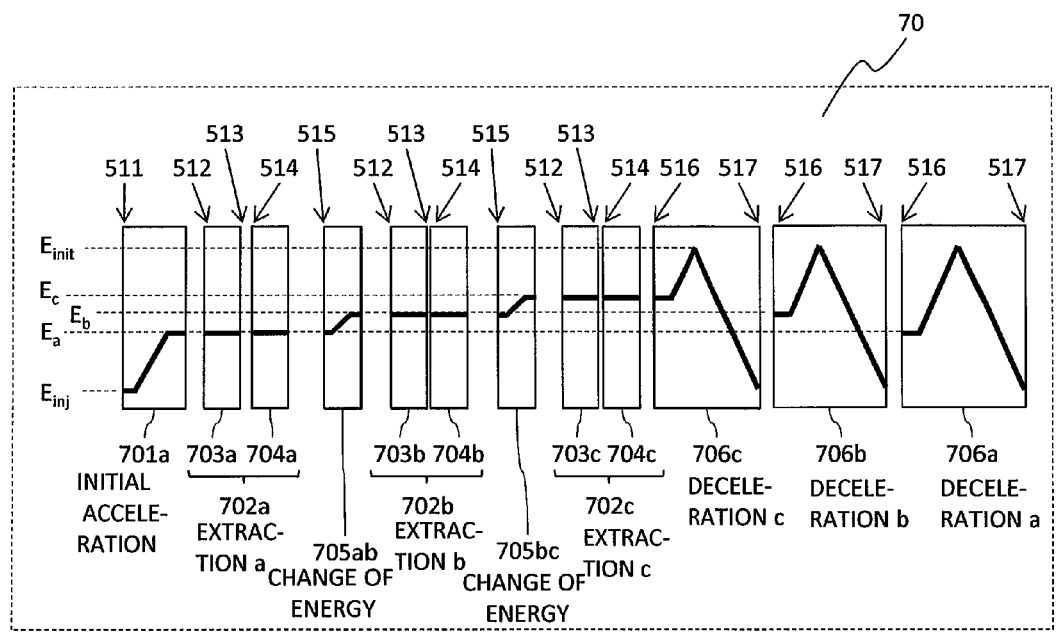
FIG. 3 is a diagram showing a structure of control data about a plural devices making up a synchrotron as one embodiment of the present invention.

FIG. 3 is a diagram showing a structure of control data (operation control data) about plural devices making up the synchrotron 13. As a representative example of the device control data, the exciting current for the bending magnet 18 is shown. With this embodiment, three stages of data are shown for purpose of explanation. In practice, as described in Non-patent Document 2, there are provided as many stages of data as the number of the energy stages of the beam for irradiation. Whereas this embodiment is shown to use the operation control data 70 whereby irradiation with the beam is performed at energy stages ranging progressively from low to high, the same effects are obtained when beam irradiation is carried out at energy stages ranging successively from high to low.

Figure 4:
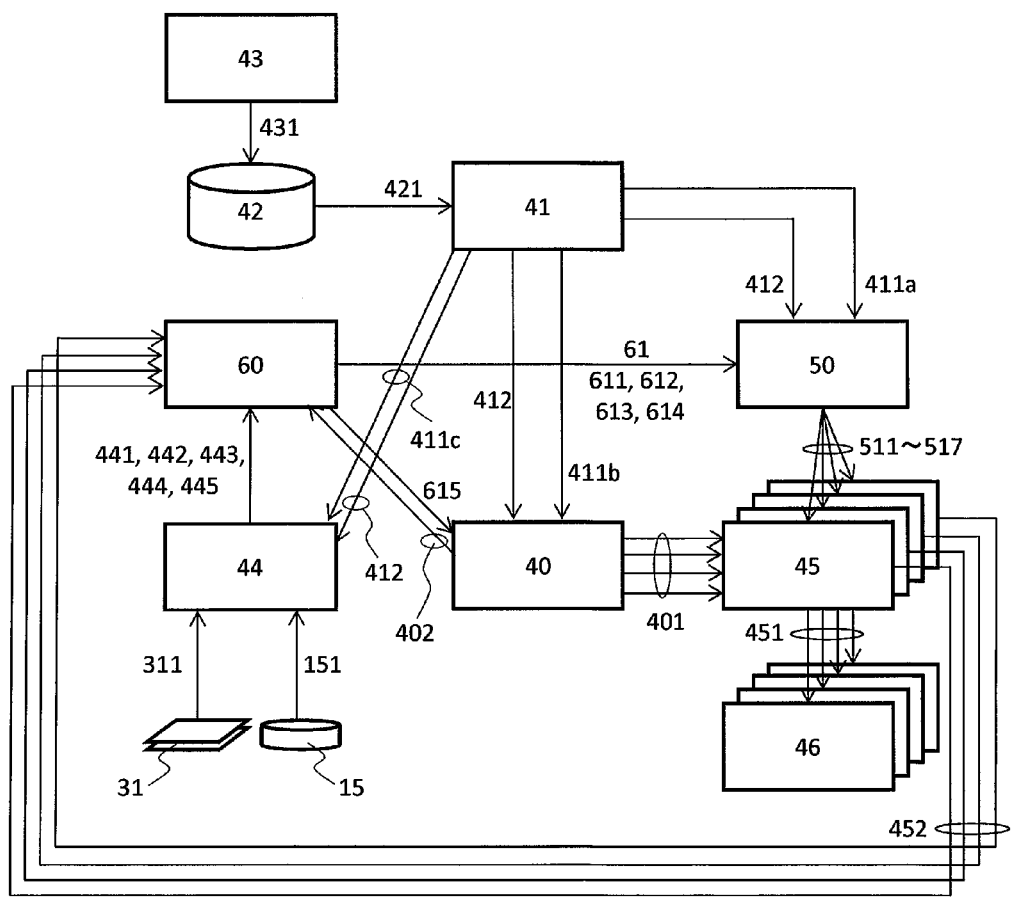
FIG. 4 is a diagram showing a configuration of a control system (controller) for implementing a multistage extraction operation as one embodiment of the present invention, the diagram also depicting how information is transferred between the devices making up the control system.
Figure 5:
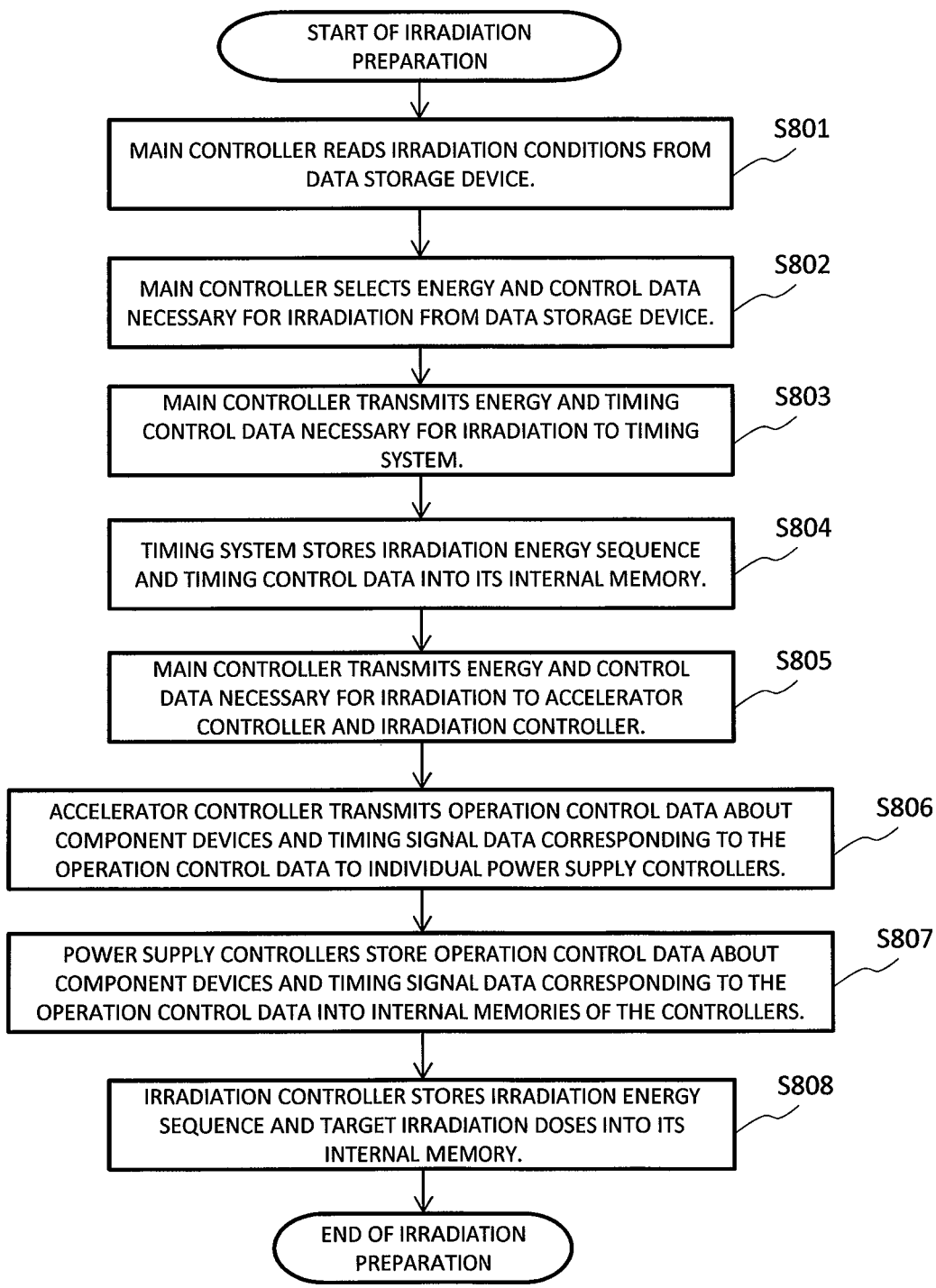
FIG. 5 is a flowchart showing an irradiation preparation flow in effect before the start of the multistage extraction operation as one embodiment of the present invention.
Figure 6:
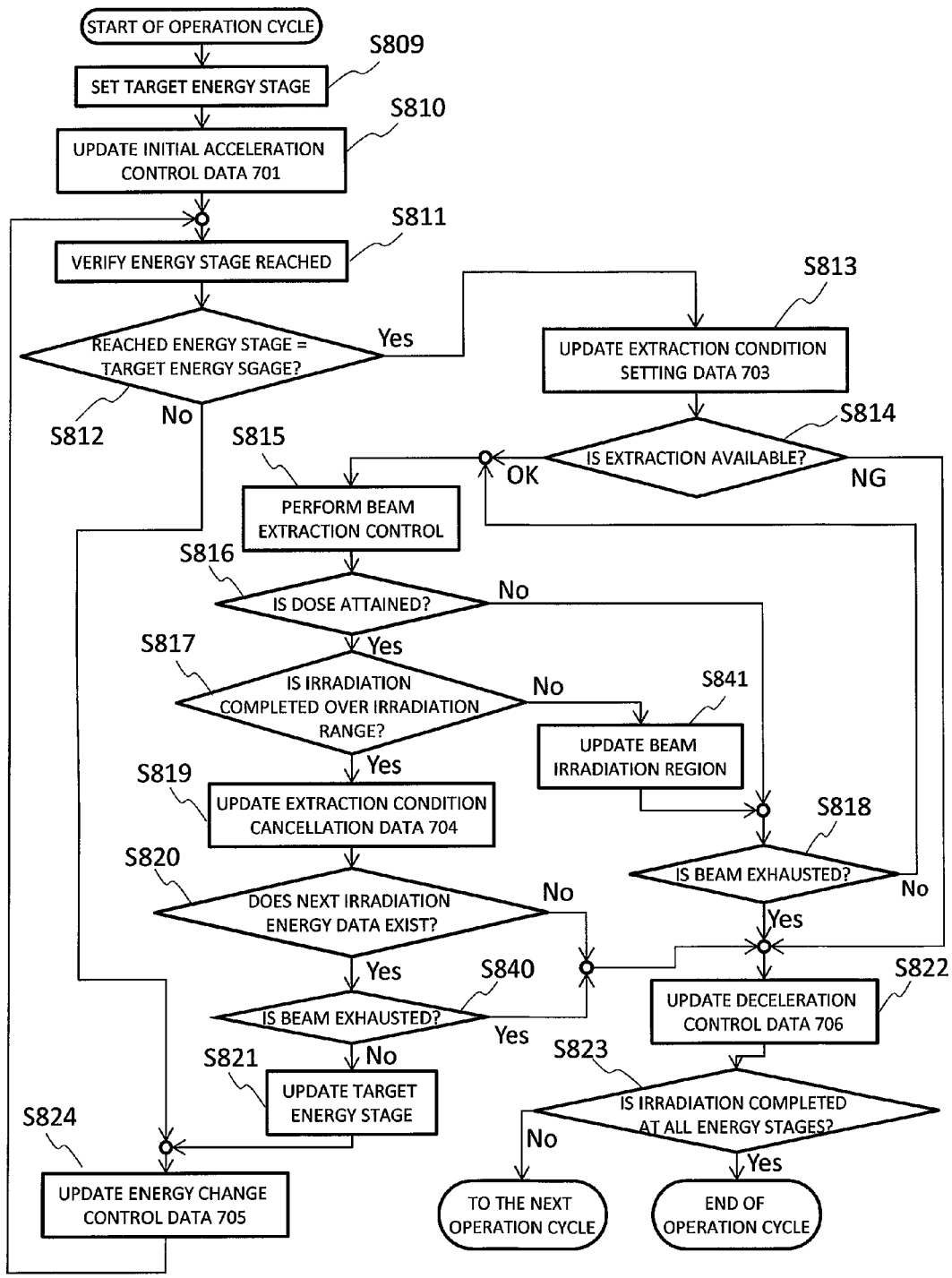
FIG. 6 is a flowchart showing a control flow in effect during the multistage extraction operation as one embodiment of the present invention.
Figure 7A:
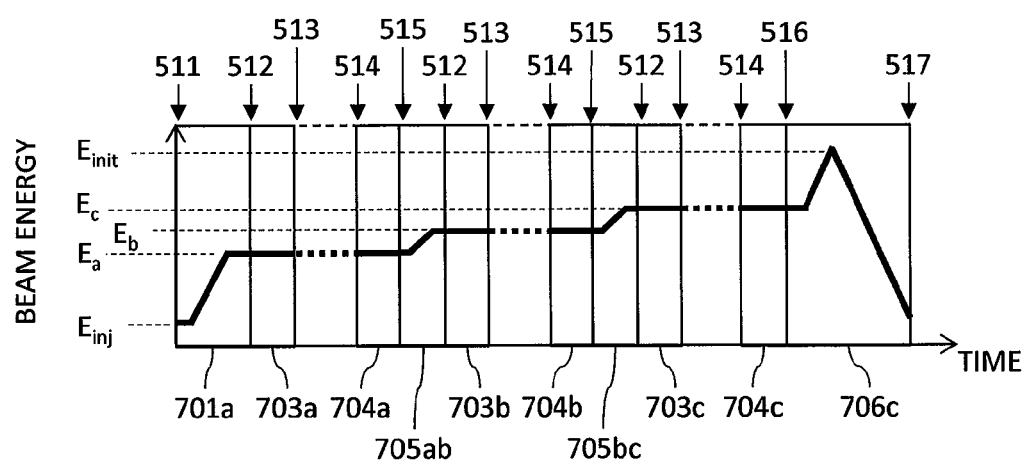
FIG. 7A is a diagram showing an example of the control data being output during the multistage extraction operation involving a combination of the control data items indicated in FIG. 3, as one embodiment of the present invention.
Figure 7B:
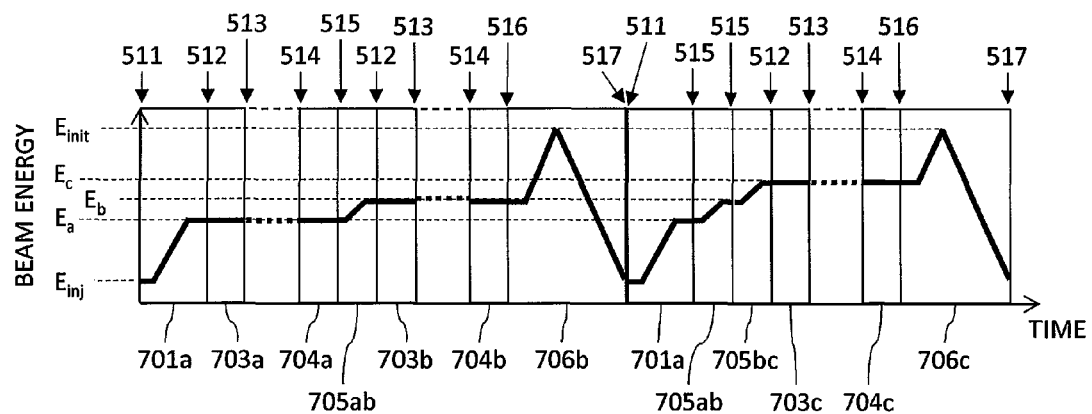
FIG. 7B is a diagram showing another example of the control data being output during the multistage extraction operation involving a combination of the control data items indicated in FIG. 3, as one embodiment of the present invention.

FIG. 4 is a diagram showing a configuration of the control system (controller) 100 for implementing the multistage extraction operation characteristic of this embodiment, the diagram also depicting how information is transferred between the devices making up the control system. FIG. 5 is a flowchart showing an irradiation preparation flow in effect before the start of the multistage extraction operation. FIG. 6 is a flowchart showing a control flow in effect during the multistage extraction operation. FIGS. 7A and 7B are diagrams showing examples of the control data being output during the multistage extraction operation involving combinations of the control data items indicated in FIG. 3.

As shown in FIG. 3, the operation control data 70 regarding the devices (bending magnet 18 in the illustrated example) constituting the synchrotron 13 are made up of an initial acceleration control data item 701a (represented by 701 hereunder), a plural extraction control data items 702a through 702c (represented by 702 hereunder) for ion beam extraction at a plural energy stages (three energy stages $E_a$, $E_b$ and $E_c$ in this example), a plural energy change control data items 705ab and 705bc (represented by 705 hereunder) connecting the plural extraction control data items 702, and a plural deceleration control data items 706a through 706c (represented by 706 hereunder) corresponding to the plural extraction control data items 702. The plural extraction control data items 702 are formed by extraction condition setting data items 703a through 703c (represented by 703 hereunder) and by extraction condition cancellation data items 704a through 704c (represented by 704 hereunder). Extraction of the beam at the plural energy stages is controlled by suitably combining these control data items. Because there are provided the deceleration control data items 706a, 706b and 706c corresponding to the plural extraction energy stages, rapid transition can be made to deceleration control from any extraction energy stage.

A target energy stage can be reached quickly from the initial acceleration control data item 701 or from the plural energy change control data items 705 connecting the plural extraction control data items 702.

A plural deceleration control data items 706a and 706b (represented by 706 hereunder where appropriate) are provided corresponding to the plural extraction control data items 702 making up the operation control data 70. These control data items 701, 702, 705 and 706 are provided as current/voltage time-series data constituting controlled variables that are fed directly to the devices involved. For example, the control data items regarding the bending magnet 18 are made up of the time-series data of exciting currents and voltages (not shown) that are set to the power supply 46B of the bending magnet 18 and needed for generating predetermined bending magnetic field intensities.

The control data items are stored in the data storage device 42. In addition to the control data items shown in FIG. 3, the data storage device 42 stores as module data the control data items for permitting beam extraction at all energy stages corresponding to the irradiation conditions for all predictable patients 36. For example, if the number of energy stages for extraction corresponding to plural predictable patients 36 is 100, the data storage device 42 stores, as the module data items, 100 initial acceleration control data items 701, 100 extraction control data items 702, 99 energy change control data items 705, and 100 deceleration control data items 706. Given the irradiation conditions of a specific patent 36 preparatory to irradiation, the main controller 41 selects the applicable control data items from among those stored in the data storage device 42 and stores the selected data items into the power supply controller 45. The module data items for permitting beam extraction at all energy stages may be stored in an internal storage device of the main controller 41.

The operation control data items 70 for multistage extraction stored beforehand in the data storage device 2 may be prepared as time-series data about the magnetic field intensity inside the synchrotron 13.

In this case, as the operation control data items 70 are being stored into the power supply controller 45 via the main controller 41 and accelerator controller 40, the data items 70 are converted at the main controller 41 or accelerator controller 40 from the time-series data about the magnetic field intensity into time-series data about exciting currents and voltages. The operation control data items 70 are thus stored into the power supply controller 45 as the time-series data about exciting currents and voltages. The power supply controller 45 outputs to the power supplies 46 power supply control command values 451 corresponding to the time-series data.

The operation control data items 70 are related individually to the timing signals 51 output from the timing system 50. The timing signals 51 of this embodiment are made up of an acceleration control start timing signal 511, an extraction condition setting timing signal 512, an extraction control wait timing signal 513, an extraction condition cancellation timing signal 514, an energy change control timing signal 515, a deceleration control start timing signal 516, and a deceleration control end timing signal 517. When the timing signal 51 is input to the power supply controller 45, the power supply controller 45 selects the control data items 701 through 706 related to the input timing signal 51 and starts data update control from the initial address of the selected control data items 701 through 706.

Explained below with reference to FIG. 3 is how update control of the operation control data items 70 is performed in response to the input timing signal 51. When the acceleration control start timing signal 511 is input, the power supply controller 45 updates the initial acceleration control data item 701a ranging from an injection energy stage ($E_{inj}$) to an initial extraction energy stage ($E_a$) in order to accelerate the beam.

When the extraction condition setting timing signal 512 is input, the extraction condition setting data items 703a are updated. Upon completion of the update of the extraction condition setting data items 703a and given the input of the extraction control wait timing signal 513, the power supply controller 45 stops the update of the extraction condition setting data items 703a. When the accelerator controller 40 applies an extraction radio frequency voltage to the radio frequency extraction electrode 20a, beam extraction control is carried out. The irradiation controller 44 successively measures the dose 311 during extraction control and, on the basis of the result of the measurement, outputs a planned dose achievement signal 442 to stop the application of the extraction radio frequency voltage and terminate extraction control. Thereafter, upon input of the extraction condition cancellation timing signal 514, the update of the extraction condition cancellation control data 704a is started. Depending on the amount of accumulated beam charge 151 upon completion of extraction control and on the existence or nonexistence of the next irradiation energy stage, the timing system 50 determines whether to make transition to energy change control (to transition from the extraction condition cancellation data 704a to the energy change control data 705ab) by outputting the energy change control timing signal 515, or whether to make transition to deceleration control (to transition from the extraction condition cancellation data 704a to the deceleration control data 706a) by outputting the deceleration control start timing signal 516. The control data items making up the operation control data 70 are arranged so that the exit value of the extraction condition cancellation data items 704 is the same as the starting value of the energy change control data items 705 for transition to the next irradiation energy stage (e.g., the exit value of 704a being equal to the starting value of 705ab in FIG. 3) and that the exit value of the extraction condition cancellation control data items 704 is the same as the starting value of the deceleration control data items for deceleration down to the injection energy stage (e.g., the exit value of 704a being equal to the starting value of 706a in FIG. 3), whereby the continuity between the control data items is ensured. When operation control is thus implemented on the basis of the input timing signals 51, it is easy to provide the changing and updating of the operation control data items 70 in accordance with the timing signals 51.

When the multistage extraction operation above is carried out, the interlock system 60 outputs an interlock signal 61 based on an energy determination signal 402 output from the accelerator controller 40; on an energy change request signal 443, a deceleration control request signal 444, and an irradiation completion signal 445 output from the irradiation controller 44; and on status information 452 output from the power supply controller 45 indicative of device integrity. The interlock signal 61 includes an energy change command 611, an extraction control command 614, an irradiation completion command 612, and a deceleration control command 613. The timing system 50 outputs the energy change control timing signal 515 on the basis of the energy change command 611 output from the interlock system 60, outputs the extraction condition setting timing signal 512 on the basis of the extraction control command 614 from the interlock system 60, outputs the extraction condition cancellation timing signal 514 on the basis of the irradiation completion command 612 from the interlock system 60, and outputs the deceleration control start timing signal 516 on the basis of the deceleration control command 613.

Explained below with reference to FIGS. 4 and 5 is the irradiation preparation flow in effect when the multistage extraction operation is performed by use of the control data shown in FIG. 3 regarding the component devices making up the synchrotron 13.

First, the treatment planning device 43 registers treatment plan information 431 including the irradiation conditions necessary for treating the patient 36 in the data storage device 42. On the basis of the setting information about the irradiation conditions, the main controller 41 reads the irradiation conditions 421 from the data storage device 42 (step S801). Given the irradiation conditions, the main controller 41 selects from the data storage device 42 the energy stages and doses necessary for irradiation, the irradiation sequence involved, and the control data (step S802). As mentioned above, the data storage device 42 stores as the module data the control data items for permitting irradiation with the beam at all energy stages corresponding to the irradiation conditions of all predictable patients 36, the control data items including the initial acceleration control data item 701, the plural extraction control data items 702, the plural extraction condition setting data items 703, the plural extraction condition cancellation data items 704, the plural energy change control data items 705, and the plural deceleration control data items 706 shown in FIG. 3. The main controller 41 selectively reads the control data items 701 through 706 on the basis of the irradiation conditions 421.

The main controller 41 transmits to the timing system 50 the energy stage information necessary for irradiation, the irradiation sequence, and timing control data 411a corresponding to the energy stages involved (step S803).

The timing system 50 stores into its memory the energy stage information necessary for irradiation, the irradiation sequence, and the timing control data 411a corresponding to the energy stages involved, all transmitted from the main controller 41 (step S804). Similarly, the main controller 41 transmits the energy stage information necessary for irradiation, the irradiation sequence, and control data items 411*b* and 411*c* corresponding to the energy stages involved to the accelerator controller 40 and irradiation controller 44 (step S805). The control data items 411*b* transmitted to the accelerator controller 40 include the operation control data items about the devices involved (control data items 701 through 706) and the timing signals corresponding to the operation control data items (timing signals 511 through 517). The control data items 411*c* transmitted to the irradiation controller 44 include the sequence of irradiation at the energy stages involved and the target doses.

The accelerator controller 40 transmits control data items 401 to the individual power supply controllers 45 of the component devices making up the synchrotron 13 and beam transport device 14 (step S806). The control data items 401 include the operation control data items about the devices (control data items 701 through 706) and the timing signals corresponding to the operation control data items (timing signals 511 through 517). The power supply controllers 45 store into their internal memories the data items 401 made up of the operation control data items about the devices and of the timing signals corresponding to the operation control data items (step S807). Thereafter, the irradiation controller 44 stores into its memory the sequence of irradiation at the energy stages involved and the target doses (step S808).

Explained below with reference to FIGS. 4 and 6 is the irradiation flow in effect when the multistage extraction operation is carried out by use of the control data items shown in FIG. 3 regarding the component devices making up the synchrotron 13.

When the user inputs an irradiation start command (not shown) to the main controller 41, the operation control of the synchrotron 13 is started. The main controller 41 outputs a control start command 412 designating the start of an operation cycle of the synchrotron 13 to the timing system 50, accelerator controller 40, and irradiation controller 44. On the basis of the control start command 412, the timing system 50, accelerator controller 40, and irradiation controller 44 set a target energy stage (step S809). In accordance with the set target energy stage, the timing system 50 sets target energy stage information on the beam about to be extracted, and the accelerator controller 40 sets the target energy stage for the individual power supply controllers. Given the target energy stage, the irradiation controller 44 sets the target doses for the dose-managed regions involved regarding the energy stage of interest.

On the basis of the control start command 412, the timing system 50 outputs the acceleration control start timing signal 511. The power supply controllers 45 start updating the initial acceleration control data item 701 (step S810).

Upon completion of initial acceleration control, the accelerator controller 40 verifies the energy stage reached after acceleration (step S811), and determines whether the energy stage reached at the end of acceleration matches the target energy stage (step S812). This determination is intended to decide whether to perform energy change control (to be discussed later) or to make immediate transition to beam extraction control, given that if the operation cycle is changed at the end of deceleration control (to be discussed later), the energy stage reached upon completion of initial acceleration control is different from the next target energy stage for extraction.

The accelerator controller 40 outputs to the interlock system 60 the energy determination signal 402 indicative of the result of the energy stage determination in step S812. If it is determined that the energy stage reached at the end of acceleration does not match the target energy stage, the interlock system 60 outputs the energy change command 611 to the timing system 50. In turn, the timing system 50 outputs the energy change control timing signal 515 to the power supply controllers 45. The power supply controllers 45 update the energy change control data items 705 (step S824).

On the other hand, if it is determined that the energy stage reached at the end of acceleration matches the target energy stage, the interlock system 60 outputs the extraction control command 614 to the timing system 50. The timing system 50 outputs the extraction condition setting timing signal 512 to the power supply controllers 45. The power supply controllers 45 start to update the extraction condition setting data items 703 (step S813).

The timing system 50 outputs the extraction control wait timing signal 513 in time with completion of the extraction condition setting data items 703 update, thereby terminating the update of the extraction condition setting data items 703 by the power supply controllers 45 and maintaining the most-recently updated values. The interlock system 60 determines whether beam extraction control is available on the basis of the status information 452 such as device integrity and energy stage verification information from the power supply controllers 45, and of an extraction control permission signal 441 output from the irradiation controller 44 based on the measurements of the amount of accumulated beam charge 151 from a remaining beam amount monitoring unit 15 in the synchrotron 13 (step S814).

If it is determined in step S814 that the control is not available ("NG"), the interlock system 60 outputs the deceleration control command 613 to the timing system 50. In turn, the timing system 50 outputs the deceleration control start timing signal 516 to the power supply controllers 45. The power supply controllers 45 update the deceleration control data items 706 (step S822).

On the other hand, if it is determined in step S814 that the control is available ("OK"), the interlock system 60 outputs an extraction permission command 615 to the accelerator controller 40. In turn, the accelerator controller 40 applies the extraction radio frequency voltage to the radio frequency extraction electrode 20*a*, thus carrying out beam extraction control (step S815).

During beam extraction control, the dose monitor 31 attached to the irradiation apparatus 30 successively measures the dose 311 of the irradiation beam, and the irradiation controller 44 calculates the cumulative dose of each dose-managed region. At this point, the irradiation controller 44 compares the cumulative dose of the dose-managed region of interest with the corresponding target dose, and determines whether the cumulative dose has reached the target dose (i.e., described as the dose "attained" hereunder; step S816).

If it is determined that the cumulative dose of the dose-managed region of interest has yet to be attained, the remaining beam amount monitoring unit 15 measures the amount of accumulated beam charge 151 in the synchrotron 13. The irradiation controller 44 determines whether the amount of accumulated beam charge 151 is sufficient for continuous beam irradiation (step S818). If it is determined that the amount of accumulated beam charge 151 in the synchrotron 13 is sufficient for continuous beam irradiation, the irradiation controller 44 continues beam extraction control.

On the other hand, if it is determined that the accumulated beam charge 151 in the synchrotron 13 is exhausted, the irradiation controller 13 outputs the deceleration control request signal 444 to the interlock system 60. In turn, the interlock system 60 outputs the deceleration control command 613 to the timing system 50. The timing system 50 outputs the deceleration control start timing signal 516 to the power supply controllers 45. The power supply controllers 45 update the deceleration control data items 706 (step S822).

On the other hand, if it determined in step S816 that the cumulative dose of the dose-managed region of interest is attained, the irradiation controller 44 determines whether irradiation is completed over the entire irradiation range at the current energy stage, i.e., on all the dose-managed regions at the current energy stage (step S817).

If it is determined that irradiation has yet to be completed on all the dose-managed regions at the current energy stage, the irradiation controller 44 using the scanning magnets 32 updates the irradiation position to reach a beam irradiation region of which the irradiation has yet to be completed, i.e., a dose-managed region of which the irradiation is not complete (step S841). Later, as in the case of step S816 in which the dose is not attained, the irradiation controller 44 determines whether the amount of accumulated beam charge 151 is sufficient for continuous beam irradiation (step S818). If it is determined that the amount of accumulated beam charge 151 in the synchrotron 13 is sufficient for continuous beam irradiation, the irradiation controller 44 carries out beam irradiation (step S815). If it is determined that the accumulated beam charge 151 in the synchrotron 13 is exhausted, the irradiation controller 44 outputs the deceleration control request signal 444 to the interlock system 60. In turn, the interlock system 60 outputs the deceleration control command 613 to the timing system 50. The timing system 50 outputs the deceleration control start timing signal 516 to the power supply controllers 45. The power supply controllers 45 update the deceleration control data items 706 (step S822).

On the other hand, if it is determined in step S817 that irradiation is completed on all dose-managed regions at the current energy stage, the irradiation controller 44 outputs the irradiation completion signal 445 to the interlock system 60. In turn, the interlock system 60 outputs the irradiation completion command 612 to the timing system 50. The timing system 50 outputs the extraction condition cancellation timing signal 514 to the power supply controllers 45. The power supply controllers 45 start to update the extraction condition cancellation data items 704 (step S819).

Upon completion of the control of updating the extraction condition cancellation data items 704, the irradiation controller 44 determines whether there is data representative of the next target energy stage (step S820). If it is determined that there exits the next target energy stage, the remaining beam amount monitoring unit 15 measures the amount of accumulated beam charge 151 in the synchrotron 13. The irradiation controller 44 determines whether the amount of accumulated beam charge 151 is sufficient for beam irradiation at the next target energy stage (step S840). If it is determined that the amount of accumulated beam charge 151 in the synchrotron 13 is sufficient for beam irradiation, the irradiation controller 44 updates the target energy stage data (step S821). On the other hand, if it is determined that the accumulated beam charge 151 in the synchrotron 13 is exhausted, controller 13 outputs the deceleration control request signal 444 to the interlock system 60. In turn, the interlock system 60 outputs the deceleration control command 613 to the timing system 50. The timing system 50 outputs the deceleration control start timing signal 516 to the power supply controllers 45. The power supply controllers 45 update the deceleration control data items 706 (step S822).

Where the irradiation range subject to dose management is minutely designated as with the spot scanning irradiation method, the process of determining the amount of accumulated beam charge 151 in step S840 may be omitted. Irradiation can be performed appropriately when the amount of accumulated beam charge 151 is determined successively as indicated in step S818.

On the other hand, where the layer is internally irradiated with a uniformly continuous beam as in raster scanning irradiation, it is preferred to perform control such that the beam will not be exhausted halfway during irradiation in order to guarantee dose uniformity and improve the dose rate. For this reason, as shown in FIG. 6, the process of step S840 is provided to determine whether the amount of accumulated beam charge 151 is sufficient for beam irradiation at the next target energy stage, before the target energy stage data is updated. If it is determined in step S840 that the amount of accumulated beam charge 151 in the synchrotron 13 is sufficient for beam irradiation, the irradiation controller 44 updates the target energy stage data (step S821) and then outputs the energy change request signal 443 to the interlock system 60. In turn, the interlock system 60 outputs the energy change command 611 to the timing system 50. The timing system 50 outputs the energy change control timing signal 515 to the power supply controllers 45. On the basis of the energy change control timing signal 515, the power supply controllers 45 update the energy change control data items 705 (step S824).

On other hand, if it is determined in step S820 that there is no data representative of the next target energy stage, i.e., that irradiation at all energy stages is completed, the irradiation controller 44 outputs the deceleration control request signal 444 to the interlock system 60. In turn, the interlock system 60 outputs the deceleration control command 613 to the timing system 50. The timing system 50 outputs the deceleration control start timing signal 516 to the power supply controllers 45. The power supply controllers 45 update the deceleration control data items 706 (step S822).

The timing system 50 outputs the deceleration control end timing signal 517 in time with completion of the update of the deceleration control data items 706. Upon input of the deceleration control end timing signal 517, the interlock system 60 determines whether irradiation at all energy stages is completed (step S823). If it is determined that irradiation at all energy stages is complete, the operation cycle is terminated.

If it is determined that transition is made to deceleration control without completing the irradiation at all energy stages (step S823), the start of the operation cycle is reached again, and initial acceleration control is restarted.

Where the start of the operation cycle is again reached and initial acceleration control is restarted, the control of updating the energy change control data items is performed until the reached energy stage matches the target energy stage (In FIG. 6, the flow of step S812→step 824→step S811→step S812 is repeated.), because the target energy stage necessary for the next round of irradiation is different from the energy stage reached under initial acceleration control. When the reached energy stage is determined to match the target energy stage, transition is made to the control of updating the extraction condition setting data items 703 (step S813).

FIGS. 7A and 7B depict examples of the control data being output during the multistage extraction operation characteristic of this embodiment. Shown in FIGS. 7A and 7B are the output examples involving the use of the output operation control data items 70 indicated in FIG. 3. Three stages of energy $E_a$, $E_b$ and $E_c$ can be extracted in one operation cycle. FIG. 7A shows changes in the exciting current of the bending magnet 18 in effect when the ion beam 10 at three energy stages ($E_a$, $E_b$ and $E_c$) is subjected to extraction control in one operation cycle. FIG. 7B shows changes in the exciting current of the bending magnet 18 in effect when, after the extraction of the ion beam 10 at two energy stages ($E_a$, $E_b$) in the initial operation cycle, an exhaustion of remaining ion beam triggers transition to deceleration control which updates the operation cycle, so that the ion beam 10 at the third energy stage ($E_c$) is extracted in the next operation cycle. Generally, the exciting current of the bending magnet 18 is approximately proportional to the beam energy. It follows that what is shown in FIGS. 7A and 7B may also be interpreted as changes in beam energy during the multistage extraction operation.

What is common to FIGS. 7A and 7B is that the timing signals 511 through 517 are set corresponding to the control data items 701 through 706. The control data items 701 through 706 are updated on the basis of the timing signals 511 through 517 being input.

First, the output example of multistage extraction control is explained with reference to FIG. 7A. When the acceleration control start timing signal 511 is input from the timing system 50, the power supply controllers 45 select the initial acceleration control data item 701 and start exciting current data update control. Upon completion of initial acceleration control, the timing system 50 inputs the extraction condition setting timing signal 512 to the power supply controllers 45. The power supply controllers 45 output the extraction condition setting data item 703a corresponding to the initial extraction energy stage $E_a$. Thereafter, upon input of the extraction control wait timing signal 513, the power supply controllers 45 maintain the most-recently updated values and carry out extraction control. Upon completion of extraction control, the timing system 50 outputs the extraction condition cancellation timing signal 514 to the power supply controllers 45. In turn, the power supply controllers 45 start updating and outputting the extraction condition cancellation data item 704a.

Upon completion of the update control of the extraction condition cancellation data item 704a, the amount of accumulated beam charge 151 inside the synchrotron 13 is measured. After determining that the amount of accumulated beam charge 151 is sufficient for beam extraction at the next energy stage, the timing system 50 outputs the energy change control timing signal 515. The power supply controllers 45 select the energy change control data item 705ab that connects the current extraction energy stage $E_a$ with the next extraction energy stage $E_b$, and start updating and outputting the control data. Thereafter, the above-described extraction condition setting control, extraction control, extraction condition cancellation control, and energy change control are repeated until the extraction control of the last energy stage $E_c$ is completed.

Upon completion of the update control of the extraction condition cancellation data item 704c at the last energy stage $E_c$, the timing system 50 outputs the deceleration control start timing signal 516. Given the input of the deceleration control start timing signal 516, the power supply controllers 45 select the deceleration control data item 706c corresponding to the preceding extraction condition cancellation data item 704c, and start updating and outputting the deceleration control data. Incidentally, since this embodiment performs beam extraction control at the energy stages ranging progressively from low to high ($E_a<E_b<E_c$), the embodiment carries out initial excitation up to a maximum energy stage ($E_{init}$) during deceleration control.

In time with the completion of deceleration control, the timing system 50 outputs the deceleration control end timing signal 517 and determines whether extraction control at all energy stages is completed. If it is determined that extraction control is complete at all energy stages, the operation cycle of the synchrotron 13 is terminated.

Explained next is the case where the operation cycle is updated during the multistage extraction operation as shown in FIG. 7B. The reference characters in FIG. 7B are the same as those in FIG. 7A. Referring to FIG. 7B, the ensuing explanation applies following the end of extraction control at the second energy stage $E_b$.

Upon completion of extraction control at the second energy stage $E_b$, the amount of accumulated beam charge 151 inside the synchrotron 13 is measured. If the result of the measurement reveals that due to beam exhaustion in particular, the amount of accumulated beam charge 151 in the synchrotron 13 is not sufficient for the next stage of beam extraction, the timing system 50 outputs the deceleration control start timing signal 516 corresponding to the energy stage at which extraction control has ended. On the basis of the deceleration control start timing signal 516 being input, the power supply controllers 45 start the update control of the deceleration control data item 706b that can connect continuously with the preceding extraction condition cancellation data item 704b.

In time with the input of the deceleration control end timing signal 517, it is determined whether extraction control at all energy stages is completed. If it is determined that extraction control at all energy stages has yet to be complete, the acceleration control start timing signal 511 is again output following the change of the target energy stage from $E_b$ to $E_c$.

Given the input of the acceleration control start timing signal 511, the update of the initial acceleration control data item 701 is started. Upon completion of initial acceleration control, a comparison is made between the energy stage reached and the target energy stage. In this case, the energy change control timing signal 515 is output, because the reached energy stage of the initial acceleration control data item 701 is $E_a$ and the target energy stage is $E_c$. On the basis of the energy change control timing signal 515, the power supply controllers 45 perform energy change control by updating the energy change control data item 705ab. After the energy change control, a comparison is again made between the energy stage reached and the target energy stage. Because the energy stage reached after energy change control is $E_b$ and the target energy stage is $E_c$, the energy change control timing signal 515 is again output and the energy change control data item 705bc is updated accordingly. This control is repeated until the reached energy stage becomes $E_c$ equal to the target energy stage through acceleration. Thereafter, the above-described extraction control and deceleration control are carried out in the same manner.

As described, this embodiment carries out the multistage extraction control operation implementing the control of changing the extraction beam energy on the synchrotron 13 by use of the control data items 701 through 706 including the deceleration control data items 706 corresponding to the plural energy stages, with rapid transition made available to deceleration control from any energy stage. Thus if an insufficient amount of accumulated beam charge 151 in the synchrotron 13 interrupts irradiation with the ion beam 10, it is possible to update the operation cycle in a short time, improve the dose rate and shorten treatment time accordingly.

If a failure in the devices making up the particle beam irradiation system has triggered interruption of the irradiation with the ion beam 10, direct transition from the extraction energy stage to deceleration control can be made, so that the operation cycle can be updated safely in a short time.

Where there remains an energy stage at which beam irradiation has yet to be performed and the operation cycle is to be updated after deceleration control is terminated typically because of an exhausted beam having interrupted beam irradiation, if the energy stage reached upon completion of initial acceleration control or energy change control does not match the next target energy stage, then energy change control is carried out immediately to accelerate the currently reached energy stage up to the target energy stage without executing the control of the extraction control data update (extraction condition setting control and extraction condition cancellation control). This makes it possible to perform energy change control in a short time, improve the dose rate and shorten treatment time.

The control data items 701 through 706 making up the operation control data 70 are constituted by use of current/voltage time-series data as controlled variables given directly to the component devices constituting the synchrotron 13. This eliminates the need for performing calculations to change parameters, so that the equipment configuration and control device arrangements are simplified.

Further, the data storage device 42 stores as module data the control data items permitting beam extraction at all energy stages corresponding to the irradiation conditions of all predictable patients 36. The main controller 41 selects the control data items 701 through 706 on the basis of the irradiation conditions 421 and stores the selected data items into the power supply controllers 45. Because the operation control data items 70 are constituted on the basis of the irradiation conditions 421, it is possible to eliminate the wasteful time that does not contribute to beam irradiation (control time ranging from injection beam energy to irradiation start energy on the synchrotron 13, and control time ranging from irradiation end energy to deceleration end energy). As a result, beam irradiation over the desired energy range can be performed in a short operation cycle, so that the dose rate is improved and treatment time is shortened.

Figure 8A:
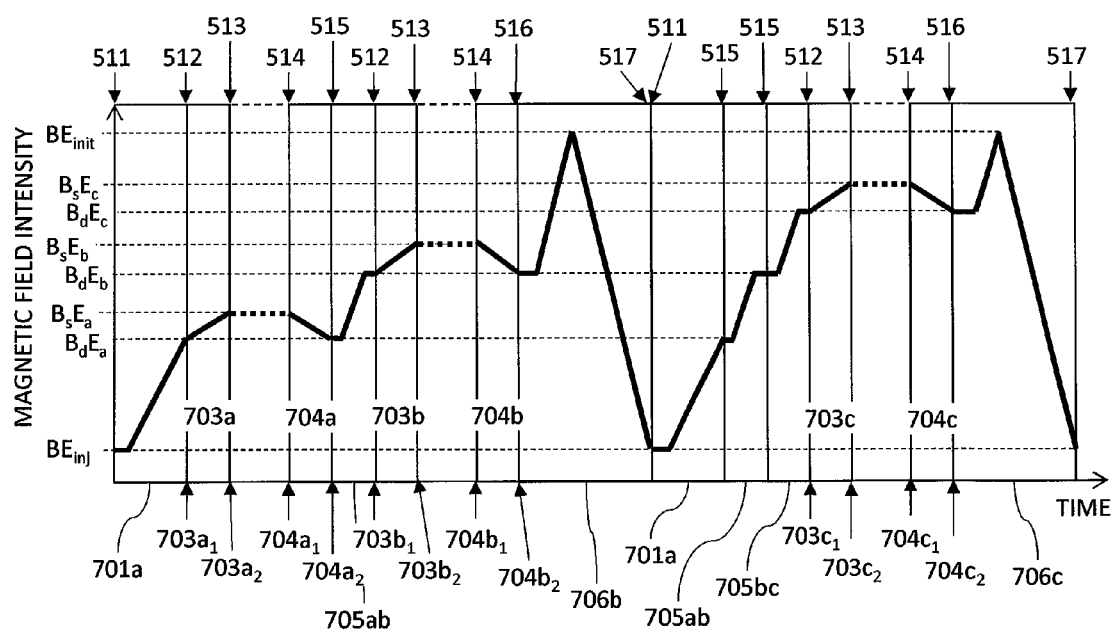
FIG. 8A is a diagram showing an example of the control data being output regarding a quadrupole magnet during the multistage extraction operation involving a combination of the control data items, as one embodiment of the present invention.
Figure 8B:
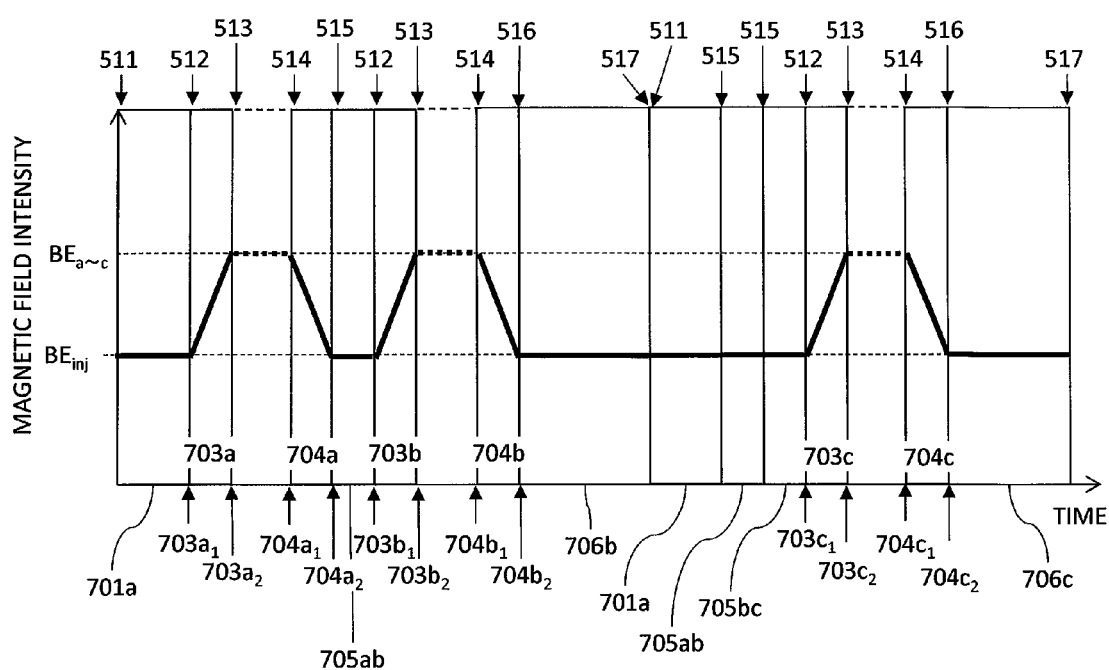
FIG. 8B is a diagram showing an example of the control data being output regarding a sextupole magnet during the multistage extraction operation involving a combination of the control data items, as one embodiment of the present invention.

FIG. 8A shows an example of the control data being output regarding the quadrupole magnet 19 of the synchrotron 13 during the multistage extraction operation, and FIG. 8B shows an example of the control data being output regarding the sextupole magnet 21 during the multistage extraction operation. The embodiment to be explained below applies where the operation control data items stored in the data storage device 42 are prepared as time-series data representative of the magnetic field intensity inside the synchrotron 13.

The quadrupole magnet 19 is set up to control the betatron oscillation frequency of particles circulating in the synchrotron 13, and the sextupole magnet 21 is provided to form a stability limit at which the particles are retrieved from the synchrotron 13.

FIG. 8A gives an operation control pattern of multistage extraction corresponding to different extraction energy stages with regard to the quadrupole magnet 19.

The particle beam irradiation system of this embodiment is provided with extraction condition data items 702 used for operation control either to bring about the state in which a beam is readied for extraction by changing the magnetic field intensity to bring the betatron oscillation frequency close to a resonance line, or to cancel that state. Also with this embodiment, the extraction condition data items 702 are divided into two data modules: extraction condition setting data items 703, and extraction condition cancellation data items 704. Further, the extraction condition data items 702 are arranged so that the starting value of the extraction condition setting data items 703 is made the same as the exit value of the extraction condition cancellation data items 704, e.g., the starting value 703a1 of 703a is made the same as the exit value 704a2 of 704a in FIG. 8A (703a1 and 704a2 being equal to the same magnetic field intensity $B_d E_a$ in FIG. 8A), so that the continuity between the data items is ensured.

Also, the exit value of the extraction condition setting data items 703 is made the same as the starting value of the extraction condition cancellation data items 704, e.g., the exit value 703a2 of 703a is made the same as the starting value 704a1 of 704a in FIG. 8A (703a2 and 704a1 being equal to the same magnetic field intensity $B_s E_a$ in FIG. 8A), so that the value between the two points is kept constant.

Implementing such control makes it possible to prevent the current command values from getting discontinued upon transition to energy change without execution of extraction control.

Whereas with this embodiment, the extraction condition setting data items 703 and extraction condition cancellation data items 704 are shown to vary linearly within their ranges in terms of magnetic field intensity, the same effects are obtained when these data items are varied continuously in terms of magnetic field intensity.

In this manner, when the starting point of the extraction condition setting data items 703 is made to coincide with the end point of the extraction condition cancellation data items 704, it is possible for the control after energy change (or initial acceleration) to guarantee the continuity of the current command values regardless of beam extraction control or energy change control being in effect. That in turn reduces the amount of calculations for ensuring the continuity of current values so that controls can be made simpler and more efficient. Also, when the end point of the extraction condition setting data items 703 is made to coincide with the starting point of the extraction condition cancellation data items 704, the continuity of the current command values is guaranteed upon switchover between control for forming the state in which the beam can be extracted on the one hand and control for canceling that state on the other hand. This also reduces the amount of calculations for ensuring the continuity of current values so that controls can be made simpler and more efficient.

In addition, no extraction conditions are set during energy change, so that beam loss can be reduced.

Furthermore, there is no need to install a quadrupole magnet (QDS) intended solely to set and cancel the extraction conditions. This helps minimize the increase in synchrotron size and lower the costs.

First, when the timing system 50 outputs the acceleration control start timing signal 511, the power supply controllers 45 select the initial acceleration control data item 701a and start the control of updating the exiting current data.

Upon completion of acceleration control, the accelerator controller 40 verifies the energy stage of the circulating ion beam 10b, and outputs the energy determination signal 402 to the interlock system 60. If the reached energy stage is found to match the target energy stage (in this case, the reached energy stage and the target energy stage are both $E_a$), the interlock system 60 outputs the extraction control command 614 to the timing system 50.

On the basis of the extraction control command 614 from the interlock system 60, the timing system 50 outputs the extraction condition setting timing signal 512. Given the extraction condition setting timing signal 512, the power supply controllers 45 update the extraction control data item 702a corresponding to the extraction energy stage $E_a$ and, within the extraction condition setting data item 703a, change the magnetic field intensity from the state $B_d E_a$ in which extraction is prepared to the state $B_s E_a$ in which extraction is available. In parallel with this, the irradiation controller 44 outputs the extraction control permission signal 441 to perform the process of applying the extraction radio frequency signal. When the extraction control wait timing signal 513 is input, the power supply controllers 45 maintain the most-recently updated values so that beam extraction control is performed.

When the dose to the affected part 37 is attained under beam extraction control, the irradiation controller 44 stops outputting the extraction control permission signal 441 and terminates the process of applying the extraction radio frequency signal. On the basis of the extraction condition cancellation timing signal 514, the power supply controllers 45 update the extraction condition cancellation data item 704a corresponding to the extraction energy stage $E_a$ and, within the extraction condition cancellation data item 704a, change the magnetic field intensity from the state $B_sE_a$ in which extraction is available to the state $B_dE_a$ in which extraction is prepared.

Consecutively, the irradiation controller 44 outputs the energy change request signal 443 to the interlock system 60 on the basis of the presence or absence of the next irradiation energy stage and the measurements of the amount of accumulated beam charge 151 in the synchrotron 13.

The interlock system 60 outputs the energy change command 611 to the timing system 50. In turn, the timing system 50 outputs the energy change control timing signal 515 to accelerate the remaining beam up to the next energy stage. On the basis of the energy change control timing signal 515, the power supply controllers 45 start the control of updating the energy change control data item 705ab corresponding to the extraction energy stage $E_b$.

Upon completion of beam acceleration based on the energy change control data item 705ab, the accelerator controller 40 verifies that the reached energy stage matches the target energy stage same as in beam extraction control of the initial extraction energy stage $E_a$. And using the extraction control data item 702b corresponding to the extraction energy stage $E_b$, the power supply controllers 45 extract the beam by changing, within the extraction condition setting data item 703b, the magnetic field intensity from the state $B_dE_b$ in which extraction is prepared to the state $B_sE_b$ in which extraction is available. After the beam is stopped, the power supply controllers 45 using the extraction condition cancellation data item 704b change the magnetic field intensity from the state $B_sE_b$ in which extraction is available to the stage $B_dE_b$ in which extraction is prepared within the data item 704b.

Upon completion of extraction control at the second extraction energy stage $E_b$, the irradiation controller 44 verifies that the next irradiation data item exists (step S820 in FIG. 6). Thereafter, the irradiation controller 44 measures the amount of accumulated beam charge 151 in the synchrotron 13. If it is determined that the measurements of the amount of accumulated beam charge 151 fail to meet the next bean extraction amount, the irradiation controller 44 transmits the deceleration control request signal 444 to the interlock system 60.

On the basis of the deceleration control request signal 444, the interlock system 60 transmits the deceleration control command 613 to the timing system 50. Upon input of the deceleration control command 613, the timing system 50 outputs the deceleration control start timing signal 516. Given the deceleration control start timing signal 516, the power supply controllers 45 select the deceleration control data item 706b corresponding to the preceding extraction energy stage $E_b$, start the control of updating the deceleration control data item 706b, and perform a change from the magnetic field intensity $BE_{init}$ corresponding to the initial energy stage ($E_{init}$) to the magnetic field intensity $BE_{inj}$ corresponding to the injection energy stage ($E_{inj}$).

After outputting the deceleration control end timing signal 517 in time with the end of the update of the deceleration control data item 706b, the timing system 50 changes the target energy stage from $E_b$ to $E_c$ because there exists the next irradiation data item, updates the operation cycle, and outputs the acceleration control start timing signal 511.

Upon input of the acceleration control start timing signal 511, the power supply controllers 45 start the control of updating the initial acceleration control data item 701a.

Upon completion of acceleration control, the accelerator controller 40 compares the reached energy stage with the target energy stage. At this point, the reached energy stage in the initial acceleration control data item 701a is $E_a$ whereas the target energy stage is $E_c$. Thus the extraction energy stages do not match ($E_a \neq E_c$).

As a result, the irradiation controller 44 does not output the extraction control permission signal 441 and does not apply the extraction radio frequency signal until the reached energy stage matches the target energy stage. Meanwhile, the timing system 50 outputs repeatedly the energy change control timing signal 515 until the target energy stage is reached. On the basis of the timing signal from the timing system 50, the power supply controllers 45 update successively the energy change control data items 705ab and 705bc.

After accelerating the beam until the reached energy stage matches the target energy stage $E_c$, the power supply controllers 45 update the extraction condition setting data item 703c corresponding to the extraction energy stage $E_c$, and change the magnetic field intensity from the state $B_dE_c$ in which extraction is prepared to the state $B_sE_c$ in which extraction is available. In parallel with this, the irradiation controller 44 outputs the extraction control permission signal 441 and performs the process of applying the extraction radio frequency signal. Upon input of the extraction control wait timing signal 513, the power supply controllers 45 maintain the most-recently updated values and extract the beam.

After the beam extraction control, the power supply controllers 45 update the extraction condition cancellation data item 704c corresponding to the extraction energy stage $E_c$ on the basis of the extraction condition cancellation timing signal 514, and change the magnetic field intensity from the state $B_sE_c$ in which extraction is available to the state $B_dE_c$ in which the extraction conditions are cancelled. Concurrently, the irradiation controller 44 verifies the next irradiation data item. Because the next irradiation energy stage does not exist (i.e., $E_c$ is the last energy stage) in this output example, the irradiation controller 44 transmits the irradiation completion signal 445 to the interlock system 60. The interlock system 60 transmits to the timing system 50 the irradiation completion command 612 indicating the absence of control of the next operation cycle. The timing system 50 outputs the deceleration control start timing signal 516. On the basis of the deceleration control start timing signal 516, the power supply controllers 45 perform transition to deceleration control.

In deceleration control, the power supply controllers 45 select the deceleration control data item 706c corresponding to the preceding extraction energy stage $E_c$ and start the control of updating the deceleration control data item 706c. The deceleration control data item 706c is updated so that in order to keep the magnetic field history of each operation cycle constant, deceleration control is performed to bring the magnetic field intensity up to $BE_{init}$ corresponding to the initial energy stage ($E_{init}$) before effecting deceleration down to $BE_{inj}$ corresponding to the injection energy stage ($E_{inj}$). In time with the end of the update of the deceleration control data item 706c, the timing system 50 outputs the deceleration control end timing signal 517 and terminates irradiation based on the irradiation completion command 612.

FIG. 8B gives an operation control pattern of multistage extraction corresponding to different extraction energy stages with regard to the sextupole magnet 21.

With the sextupole magnet 21, the plural extraction control data items 702 are also divided into the extraction condition setting data items 703 and the extraction condition cancellation data items 704.

The extraction condition data items 702 are further arranged so that the starting value of the extraction condition setting data items 703 is made the same as the exit value of the extraction condition cancellation data items 704, e.g., the starting value 703a1 of 703a is made the same as the exit value 704a2 of 704a in FIG. 8B (703a1 and 704a2 being equal to the same magnetic field intensity $BE_{inj}$ in FIG. 8B), so that the continuity between the data items is ensured. Also, the exit value of the extraction condition setting data items 703 is made the same as the starting value of the extraction condition cancellation data items 704, e.g., the exit value 703a2 of 703a is made the same as the starting value 704a1 of 704a in FIG. 8B (703a2 and 704a1 being equal to the same magnetic field intensity $BE_a$ in FIG. 8B), so that the value between the two points is kept constant.

Implementing such control makes it possible to reduce beam loss attributable to the current command values getting discontinued upon energy change without execution of extraction control.

Whereas with this embodiment, the extraction condition setting data items 703 and extraction condition cancellation data items 704 are shown to vary linearly within their ranges in terms of magnetic field intensity, the same effects are obtained when these data items are varied continuously in terms of magnetic field intensity.

In this manner, when the starting point of the extraction condition setting data items 703 is made to coincide with the end point of the extraction condition cancellation data items 704, it is possible for the control after energy change (or initial acceleration) to guarantee the continuity of the current command values regardless of beam extraction control or energy change control being in effect. That in turn reduces the amount of calculations for ensuring the continuity of current values so that controls can be made simpler and more efficient. Also, when the end point of the extraction condition setting data items 703 is made to coincide with the starting point of the extraction condition cancellation data items 704, the continuity of the current command values is guaranteed upon switchover between control for forming the state in which the beam can be extracted on the one hand and control for canceling that state on the other hand. This also reduces the amount of calculations for ensuring the continuity of current values so that controls can be made simpler and more efficient.

In addition, no extraction conditions are set during energy change, so that beam loss can be reduced.

First, when the timing system 50 outputs the acceleration control start timing signal 511, the power supply controllers 45 select the initial acceleration control data item 701a and start the control of updating the exiting current data.

Upon completion of acceleration control, the accelerator controller 40 verifies the energy stage of the circulating ion beam 10b, and outputs the energy determination signal 402 to the interlock system 60. If the reached energy stage is found to match the target energy stage (in this case, the reached energy stage and the target energy stage are both $E_a$), the interlock system 60 outputs the extraction control command 614 to the timing system 50.

On the basis of the extraction control command 614 from the interlock system 60, the timing system 50 outputs the extraction condition setting timing signal 512. Given the extraction condition setting timing signal 512, the power supply controllers 45 update the extraction control data item 702a corresponding to the extraction energy stage $E_a$ and, within the extraction condition setting data item 703a, change the magnetic field intensity from the state $BE_{inj}$ in which extraction is prepared to the state $BE_a$ in which extraction is available. In parallel with this, the irradiation controller 44 outputs the extraction control permission signal 441 to perform the process of applying the extraction radio frequency signal. When the extraction control wait timing signal 513 is input, the power supply controllers 45 maintain the most-recently updated values so that beam extraction control is performed.

When the dose to the affected part 37 is attained under beam extraction control, the irradiation controller 44 stops outputting the extraction control permission signal 441 and terminates the process of applying the extraction radio frequency signal. On the basis of the extraction condition cancellation timing signal 514, the power supply controllers 45 update the extraction condition cancellation data item 704a corresponding to the extraction energy stage $E_a$ and, within the extraction condition cancellation data item 704a, change the magnetic field intensity from the state $BE_a$ in which extraction is available to the state $BE_{inj}$ in which extraction is prepared.

Consecutively, the irradiation controller 44 outputs the energy change request signal 443 to the interlock system 60 on the basis of the presence or absence of the next irradiation energy stage and the measurements of the amount of accumulated beam charge 151 in the synchrotron 13.

The interlock system 60 outputs the energy change command 611 to the timing system 50. In turn, the timing system 50 outputs the energy change control timing signal 515 to accelerate the remaining beam up to the next energy stage. On the basis of the energy change control timing signal 515, the power supply controllers 45 start the control of updating the energy change control data item 705ab corresponding to the extraction energy stage $E_b$.

Upon completion of beam acceleration based on the energy change control data item 705ab, the accelerator controller 40 verifies that the reached energy stage matches the target energy stage same as in beam extraction control of the initial extraction energy stage $E_a$. Using the extraction control data item 702b corresponding to the extraction energy stage $E_b$, the power supply controllers 45 extract the beam by changing, within the extraction condition setting data item 703b, the magnetic field intensity from the state $BE_{inj}$ in which extraction is prepared to the state $BE_b$ in which extraction is available. After the beam is stopped, the power supply controllers 45 using the extraction condition cancellation data item 704b change the magnetic field intensity from the state $BE_b$ in which extraction is available to the stage $BE_{inj}$ in which extraction is prepared within the data item 704b.

Upon completion of extraction control at the second extraction energy stage $E_b$, the irradiation controller 44 verifies that the next irradiation data item exists (step S820 in FIG. 6). Thereafter, the irradiation controller 44 measures the amount of accumulated beam charge 151 in the synchrotron 13. If it is determined that the measurements of the amount of accumulated beam charge 151 fail to meet the next bean extraction amount, the irradiation controller 44 transmits the deceleration control request signal 444 to the interlock system 60.

On the basis of the deceleration control request signal 444, the interlock system 60 transmits the deceleration control command 613 to the timing system 50. Upon input of the deceleration control command 613, the timing system 50 outputs the deceleration control start timing signal 516. Given the deceleration control start timing signal 516, the power supply controllers 45 select the deceleration control data item 706b corresponding to the preceding extraction energy stage $E_b$, and start the control of updating the deceleration control data item 706b.

After outputting the deceleration control end timing signal 517 in time with the end of the update of the deceleration control data item 706b, the timing system 50 changes the target energy stage from $E_b$ to $E_c$ because there exists the next irradiation data item, updates the operation cycle, and outputs the acceleration control start timing signal 511.

Upon input of the acceleration control start timing signal 511, the power supply controllers 45 start the control of updating the initial acceleration control data item 701a.

Upon completion of acceleration control, the accelerator controller 40 compares the reached energy stage with the target energy stage. At this point, the reached energy stage in the initial acceleration control data item 701a is $E_a$ whereas the target energy stage is $E_c$. Thus the extraction energy stages do not match ($E_a \neq E_c$).

As a result, the irradiation controller 44 does not output the extraction control permission signal 441 and does not apply the extraction radio frequency signal until the reached energy stage matches the target energy stage. Meanwhile, the timing system 50 outputs repeatedly the energy change control timing signal 515 until the target energy stage is reached. On the basis of the timing signal from the timing system 50, the power supply controllers 45 update successively the energy change control data items 705ab and 705bc.

After accelerating the beam until the reached energy stage matches the target energy stage $E_c$, the irradiation controller 44 outputs the extraction control permission signal 441. On the basis of the extraction condition setting timing signal 512, the power supply controllers 45 update the extraction condition setting data item 702c corresponding to the extraction energy stage $E_c$ and perform the process of applying the extraction radio frequency signal by changing, within the extraction condition setting data item 703c, the magnetic field intensity from the state $BE_{inj}$ in which extraction is prepared to the state $BE_c$ in which extraction is available. Upon input of the extraction control wait timing signal 513, the power supply controllers 45 maintain the most-recently updated values and extract the beam. After the beam extraction control, the power supply controllers 45 update the extraction condition cancellation data item 704c corresponding to the extraction energy stage $E_c$ on the basis of the extraction condition cancellation timing signal 514, and change the magnetic field intensity from the state $BE_c$ in which extraction is available to the state $BE_{inj}$ in which the extraction conditions are cancelled. Concurrently, the irradiation controller 44 verifies the next irradiation data item. Because the next irradiation energy stage does not exist (i.e., $E_c$ is the last energy stage) in this output example, the irradiation controller 44 transmits the irradiation completion signal 445 to the interlock system 60. The interlock system 60 transmits to the timing system 50 the irradiation completion command 612 indicating the absence of control of the next operation cycle. The timing system 50 outputs the deceleration control start timing signal 516. On the basis of the deceleration control start timing signal 516, the power supply controllers 45 perform transition to deceleration control.

In deceleration control, the power supply controllers 45 select the deceleration control data item 706c corresponding to the preceding extraction energy stage $E_c$ and start the control of updating the deceleration control data item 706c. In time with the end of the update of the deceleration control data item 706c, the timing system 50 outputs the deceleration control end timing signal 517 and terminates irradiation based on the irradiation completion command 612.

According to this embodiment, as explained above, the operation control data about the component device constituting the synchrotron are structured to include an initial acceleration control data item, a plural extraction control data items corresponding to a plural energy stages for extraction from the synchrotron, a plural energy change control data items that connect the plural extraction control data items, and a plural deceleration control data items corresponding to the plural extraction control data items. The plural extraction control data items are arranged to include extraction condition setting data items for shifting the magnetic field intensity from the state suitable for beam acceleration and deceleration to the state fit for beam extraction, and extraction condition cancellation data items for returning the magnetic field intensity from the state fit for beam extraction to the state suitable for beam acceleration and deceleration.

Further, the starting point of the extraction condition setting data items is made to coincide with the end point of the extraction condition cancellation data items, and the end point of the extraction condition setting data items is made to coincide with the starting point of the extraction condition cancellation data items.

When these control data items are suitably combined to permit beam extraction control at the plural energy stages, it is possible to shorten the time required to reach the desired energy stages, reduce beam loss during energy change intervals, and improve the dose rate thereby to shorten treatment time.

As described, beam energy change control and operation cycle update can be implemented in a short time.

It might happen that in any of the above-mentioned combinations of the operation control data items, the desired extraction energy stage differs from the energy stage reached following energy change control including initial acceleration control. In that case, the energy change control data items are connected until the desired extraction energy stage is reached.

This makes it possible to reach the desired extraction energy stage in a short time, improve the dose rate and thereby shorten treatment time.

Also according to the present invention, there is no need to install a quadrupole magnet (QDS) for setting and canceling the extraction conditions in multistage extraction control. This helps minimize the increase in synchrotron size and, with the existing magnets and power supplies suitable used, lower the costs.

It should be understood that the present invention when embodied is not limited to the above-described embodiment and that various modifications, variations and alternatives may be made of the invention so far as they are within the spirit and scope of the appended claims. The embodiment is given as a detailed, comprehensive explanation of the present invention. The invention is thus not limited to any embodiment containing all components explained above.

What is claimed is:

1. A particle beam irradiation system comprising:
a synchrotron accelerating an ion beam and having the accelerated ion beam extracted therefrom;
an irradiation device for executing irradiation with the ion beam extracted from the synchrotron; and
a controller programmed to control component devices constituting the synchrotron to extract the ion beam at a plurality of energy stages according to a combination of at least one initial acceleration control data item, a plurality of extraction control data items for ion beam extraction at a plurality of energy stages, a plurality of energy change control data items connecting the plurality of extraction control data items, and a plurality of deceleration control data items corresponding to the plurality of extraction control data items, wherein
the controller holds, as the plurality of extraction control data items, extraction condition setting data items for setting extraction conditions and extraction condition cancellation data items for canceling the extraction conditions.

2. The particle beam irradiation system according to claim 1, wherein the plurality of extraction control data items are arranged in such a manner that the initial value of the extraction condition setting data items is the same as the final value of the extraction condition cancellation data items and that the final value of the extraction condition setting data items is the same as the initial value of the extraction condition cancellation data items.

3. The particle beam irradiation system according to claim 1, wherein the extraction condition setting data items and the extraction condition cancellation data items constituting the plural extraction control data items are used to control a quadrupole magnet and a sextupole magnet positioned in the synchrotron.

4. An operating method for a particle beam irradiation system having a synchrotron accelerating an ion beam and having the accelerated ion beam extracted therefrom; and an irradiation device for executing irradiation with the ion beam extracted from the synchrotron, the operating method comprising:

controlling component devices constituting the synchrotron to extract the ion beam at a plurality of enemy stages according to a combination of at least one initial acceleration control data item, a plurality of extraction control data items for ion beam extraction at a plurality of energy stages, a plurality of energy change control data items connecting the plurality of extraction control data items, and a plurality of deceleration control data items corresponding to the plurality of extraction control data items having the deceleration control data items arranged to correspond to the energy stages so that transition can be made rapidly to deceleration control from any energy stage; and allowing extraction condition setting data items for setting extraction conditions and extraction condition cancellation data items for canceling the extraction conditions to be used as the plural extraction control data items.

* * * * *